(12) United States Patent
Cheng et al.

(10) Patent No.: US 11,459,302 B2
(45) Date of Patent: Oct. 4, 2022

(54) REFINING PROCESS AND REFINING SYSTEM OF CAPROLACTAM

(71) Applicant: ZHEJIANG HENGYI PETROCHEMICAL RESEARCH INSTITUTE CO., LTD., Hangzhou (CN)

(72) Inventors: Shibiao Cheng, Zhejiang (CN); Songlin Wang, Zhejiang (CN); Fei Shen, Zhejiang (CN); Han Wang, Zhejiang (CN); Xi Li, Zhejiang (CN); Xinping Zhang, Zhejiang (CN); Dejia Ma, Zhejiang (CN); Xiaokang Hu, Zhejiang (CN); Zong Li, Zhejiang (CN); Yixuan He, Zhejiang (CN)

(73) Assignee: ZHEJIANG HENGYI PETROCHEMICAL RESEARCH INSTITUTE CO., LTD., Hangzhou (CN)

( * ) Notice: Subject to any disclaimer, the term of this patent is extended or adjusted under 35 U.S.C. 154(b) by 74 days.

(21) Appl. No.: 17/208,073

(22) Filed: Mar. 22, 2021

(65) Prior Publication Data

US 2022/0089545 A1 Mar. 24, 2022

(30) Foreign Application Priority Data

Sep. 22, 2020 (CN) .......................... 202011003857.0

(51) Int. Cl.
*C07D 201/06* (2006.01)
*C07D 201/16* (2006.01)
*C07D 223/10* (2006.01)

(52) U.S. Cl.
CPC ................................ *C07D 223/10* (2013.01)

(58) Field of Classification Search
CPC ... C07D 201/06; C07D 201/16; C07D 223/10
See application file for complete search history.

(56) References Cited

FOREIGN PATENT DOCUMENTS

| CN | 1263091 A | 8/2000 |
|---|---|---|
| CN | 1332158 A | 1/2002 |
| CN | 101070298 A | 11/2007 |
| CN | 101070299 A | 11/2007 |
| CN | 109665981 A | 4/2019 |
| CN | 109721520 A | 5/2019 |
| CN | 109721537 A | 5/2019 |

*Primary Examiner* — Brenda L Coleman
(74) *Attorney, Agent, or Firm* — Sughrue Mion, PLLC

(57) ABSTRACT

A refining process includes steps of subjecting crude caprolactam to a first evaporative crystallization and a first solid-liquid separation to obtain a first caprolactam crystal and a first crystallization mother liquor; washing the first caprolactam crystal to obtain a second caprolactam crystal; optionally concentrating the first crystallization mother liquor to perform a second evaporative crystallization and a second solid-liquid separation to obtain a third caprolactam crystal and a second crystallization mother liquor; subjecting the third caprolactam crystal to a second washing to obtain a fourth caprolactam; optionally concentrating the second crystallization mother liquor to perform thermostatic crystallization, performing separation to obtain a fifth caprolactam crystal and a third crystallization mother liquor; washing the fifth caprolactam crystal to obtain a sixth caprolactam crystal; and subjecting the second caprolactam crystal to a hydrogenation reaction.

20 Claims, 1 Drawing Sheet

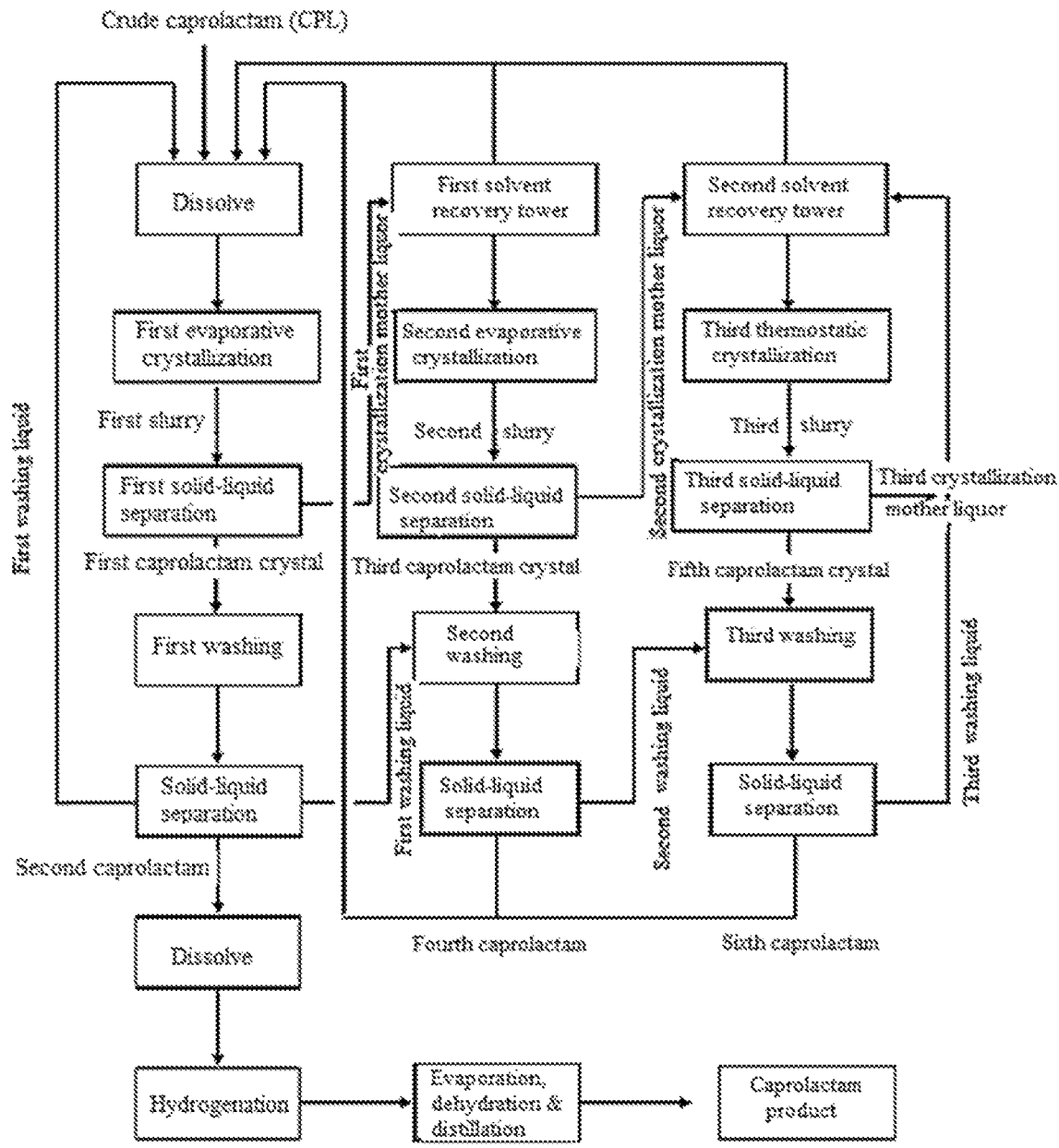

REFINING PROCESS AND REFINING SYSTEM OF CAPROLACTAM

CROSS REFERENCE TO RELATED APPLICATIONS

The Application claims priority to Chinese Application No. 202011003857.0, filed on Sep. 22, 2020, entitled "Refining Process and Refining System of Caprolactam", which is herein specially and entirely incorporated by reference.

FIELD

The present disclosure relates to the field of caprolactam production, and particularly to a refining process and a refining system of caprolactam.

BACKGROUND

Caprolactam is one of the major raw materials for synthetic fiber and synthetic resin, and mainly used for the manufacture of polyamide fibers (nylon 6), resins, thin films and the like. The current industrial production methods of caprolactam are mainly consisting of the oxidation process of cyclohexane, and partial hydrogenation process of benzene, and the photonitrosation process, wherein 90% of the manufacturing processes are subjected to the Beckmann rearrangement of cyclohexanone oxime. The preparation of caprolactam from cyclohexanone oxime primarily uses the liquid phase Beckmann rearrangement process, while the Sumitomo Corporation in Japan has adopted a novel technology of gas phase Beckmann rearrangement of cyclohexanone oxime.

The liquid phase Beckmann rearrangement relates to the Beckmann rearrangement reaction performed under the catalytic action of the fuming sulfuric acid, the reactant is further neutralized with ammonia to produce caprolactam and ammonium sulfate. The process has been industrialized for a long time, is currently the most widely used caprolactam production process in the world due to its advantages of mature technology and stable product quality. However, the process suffers from disadvantages such as corrosion of equipment, environmental pollution, economic inefficiencies and generating a large amount of ammonium sulfate as the by-product.

The gas phase Beckmann rearrangement reaction of cyclohexanone oxime under the solid acid catalyst condition is a novel process for producing caprolactam in an environmentally-friendly manner without generating the byproduct ammonium sulfate, the process does not have the defects with respect to corrosion of equipment and environmental pollution, and the separation and purification process of products is greatly simplified. Therefore, the novel process for the gas phase Beckmann rearrangement reaction for producing caprolactam in an environmentally-friendly manner without generating the byproduct ammonium sulfate have attracted widespread attention from the industry insiders. The gas phase Beckmann rearrangement reaction has a high reaction temperature, both the cyclohexanone oxime and caprolactam have poor thermal stability, and the reaction solvent methanol is relatively active, thus the reaction is generally accompanied with a plurality of side reactions such as cracking, hydrolysis, alcoholysis, hydrogenation, dehydrogenation, oxidization, thermal condensation and Mannich reaction, and generates a large variety of byproducts including more than forty identified by-products and dozens of unidentified by-products. The selectivity of the gas phase rearrangement reaction is only about 96.5%. In general, the crude caprolactam obtained after distillation has a purity of 98-99.6%, and contains 0.4-2% of other impurities.

It is well-known in the art that the caprolactam is a feedstock for producing polyamide, thus there is a high quality requirement for caprolactam products which are utilized for preparing polyamide and further used for producing synthetic fibers and synthetic resins. The impurities with a content level of $\mu g/g$ will affect the subsequent polymerization of caprolactam, cause that the filament yarns cannot be easily formed, and is prone to cause oxidization or colorimetric change. Therefore, it is necessary to obtain the crude product of caprolactam through a variety of separation and purification methods, and then utilize a variety of refining methods to finally produce caprolactam with a high purity, and such a caprolactam with a high purity can be used for producing synthetic fibers, synthetic resins, thin films and other products.

However, the separation and purification methods using extraction, distillation and ion exchange cannot sufficiently remove impurities having similar chemical properties with caprolactam, or by-products having proximate boiling points with caprolactam. In such a circumstance, hydrogenation is a highly effective means. The hydrogenation reaction is effective for increasing potassium permanganate absorption value of the product. While in the current purification processes, a typical separation and purification method such as distillation, extraction, ion exchange, adsorption and hydrogenation, alone or in combination, does not ensure that the caprolactam purity can meet the requirement of the industrially desirable product.

The use of crystallization method for the preparation of chemical substances with high purity is one of the oldest and efficient separation methods, and has been preferred by the industry due to its characteristics of low energy consumption, less contamination and high separation efficiency. It is one of the specific techniques for the preparation of organic compounds having a high purity, and has been an important means for separating the complex organic mixtures. The crystallization of crude caprolactam refers to the precipitation process of caprolactam from the liquid phase in a form of the caprolactam crystal. The polymer grade caprolactam is a thermosensitive substance and requires a low level of impurities, thus the separation and purification process through crystallization has attracted considerable attention from the major production companies of caprolactam. The refining processes of caprolactam associated with crystallization have been developed successively by the Bayer Company in Germany, the INVENT in Switzerland, the DSM in Netherland, and Sumitomo Corporation in Japan. The crystallization processes are composed of crystallization in water, crystallization in an organic solvent, and solvent-free crystallization, wherein the product obtained from the solvent-free crystallization has a small particle size, and suffers from serious scale formation, which causes difficulties for the continuous operation in the industrial scale, and obstructs the development of crystallization process.

In the research process of caprolactam crystallization, it has been discovered by the researchers that a particular phenomenon of liquid-liquid phase separation exists when the crystallization is carried out under the specific conditions of a mutually soluble solvent system. The liquid-liquid phase separation phenomenon is called an oil precipitation phenomenon. When the oil precipitation phenomenon occurs, the caprolactam component is enriched and precipitates out of the mother liquor to shape an oil phase, and forms a thermodynamically equilibrium system with the remaining mother liquor. The oil precipitation phenomenon in the field of caprolactam crystallization has attracted great concern from the industry in the recent years.

From the perspective of the crystallization phenomenon, both the oil precipitation and the crystal nucleation will lead to a decreased turbidity of the solution, it is difficult to distinguish the oil precipitation and the crystal nucleation by visual inspection or nephelometer instrument detection under the constant stirring condition, the oil droplets and crystals are often distinguished by standing still and layering of the suspension liquid in the laboratory studies. During the research process of caprolactam, oil precipitation is rarely observed in the research or production processes because of the difficulty for static observation of the crystal suspension liquid on the one hand, and the lack of on-line analysis and monitoring means in regard to the crystallization process on the other hand; when the occurrence of an oil precipitation phenomenon results in a degrading of the product quality, the researches or production personnel often attribute the quality problem to the batch-to-batch discrepancy, thus there is no much attention on the thermodynamic and kinetic characteristics of the oil precipitation phenomenon during the crystallization process, the influencing mechanism of the oil precipitation phenomenon on the industrial crystallization production process and the quality of the crystalline product, as well as the effective control targeting on the oil precipitation process.

CN1263091A discloses a process for purifying caprolactam comprising the following steps: crystallizing caprolactam from a hydrocarbon solution comprising a crude caprolactam; and contacting the crystallized caprolactam with hydrogen in the presence of a hydrogenation catalyst.

CN1332158A discloses a process for preparing caprolactam comprising the following steps: (i) pouring a molten crude caprolactam and a solvent comprising an aliphatic hydrocarbon and having a temperature lower than that of crude caprolactam, into a container and mixing the caprolactam and solvent to obtain a first slurry containing a crystallized caprolactam; and (ii) subjecting the slurry to a solid-liquid separation to obtain caprolactam and a first liquid phase.

In the patent applications CN101070298A, CN101070299A and CN1263091A, the oil precipitation phenomenon has been observed in each process of using the n-heptane, n-octane, and isooctane alone as the crystallization solvent of caprolactam. In addition, caprolactam crystallization and refining are performed by using a mixed solvent consisting of cyclohexane and n-heptane (at a weight ratio of 1:3), an oil precipitation phenomenon is not observed in the primary line crystallization, but the oil precipitation phenomenon is observed in the second crystallization of the crystallization mother liquid obtained after subjecting the crystallization slurry to a solid-liquid separation, it seriously affects the caprolactam product quality.

CN109721520A discloses a caprolactam refining method comprising the following steps: (1) carrying out vacuum distillation on a crude caprolactam product containing impurities with a boiling point higher than the boiling point of caprolactam and impurities with a boiling point lower than the boiling point of caprolactam to remove the impurities with the boiling point lower than the boiling point of caprolactam, so that a light component removed product is obtained; (2) mixing the light component removed product with a crystallization solvent, and then carrying out crystallizing to obtain a crystal; and (3) carrying out a hydrogenation reaction on the crystal, wherein a crystallization solvent contains a solvent A and a solvent B. At 20° C., the solubility of caprolactam in the solvent A is 25 wt % or above, the solubility of caprolactam in the solvent B is 5 wt % or below, and the mass ratio of the solvent A to the solvent B is 1:(1-50). The addition amount of solvent A in the patent application is 2% or more, which seriously affects the yield of caprolactam.

CN109665981A discloses a caprolactam preparation method comprising the following steps: carrying out a gas phase Backman rearrangement reaction on cyclohexanone oxime to obtain a crude caprolactam product, and crystallizing the crude caprolactam product, wherein the solvent used by the crystallization contains a solvent A and a solvent B, the solubility of caprolactam in the solvent A at a temperature of 20° C. is more than 25 wt %, the solubility of caprolactam in the solvent B is less than 5 wt %, a mass ratio of the solvent A to the solvent B is 1:(1-50). The solvent A of the patent application is 2.5% or more, which also seriously affects the yield of caprolactam, and the caprolactam yield is lower.

CN109721537A discloses a caprolactam refining method comprising the following steps: (1) performing vacuum distillation in regard to a crude caprolactam product containing impurities with a boiling point higher than the boiling point of caprolactam and impurities with a boiling point lower than the boiling point of caprolactam, so as to remove impurities with the boiling point lower than the boiling point of caprolactam, and obtain a light component removed product; (2) mixing the light component removed product with a crystallization solvent, and then carrying out crystallizing to obtain a crystal; and (3) subjecting the crystal to a hydrogenation reaction, wherein the vacuum distillation is carried out under a condition of variable temperature and variable pressure, and the mass ratio of the crystallization solvent to the light removed product is (0.2-5):1. The patent application uses ethers and/or hydrocarbons as crystallization solvents.

Although the aforementioned methods have purified the crude caprolactam product to a certain degree, but the chroma of caprolactam is not ideal, the methods provided by the prior art cannot produce the high yield and high quality of caprolactam.

SUMMARY

The present disclosure aims to overcome the problems in the prior art that the yield and quality of caprolactam need for further improvement, and the high yield and high quality of caprolactam cannot be obtained simultaneously, and provides a refining process and a refining system of caprolactam. The caprolactam prepared and obtained with the refining process has higher yield and optimal quality, especially an improved caprolactam quality.

In order to achieve the above object, the present disclosure provides a process for refining caprolactam, wherein the process comprises the following steps:

(1) subjecting a crude caprolactam having a caprolactam content not less than 98 wt % to a first evaporative crystallization in the presence of a first crystallization solvent, so as to obtain a first slurry;

(2) subjecting the first slurry to a first solid-liquid separation to obtain a first caprolactam crystal and a first crystallization mother liquor;

(3) subjecting the first caprolactam crystal to a first washing to obtain a second caprolactam crystal and a first washing liquid;

(4) optionally concentrating the first crystallization mother liquor and then subjecting the concentrated first crystallization mother liquor to a second evaporative crystallization to obtain a second slurry;

(5) subjecting the second slurry to a second solid-liquid separation to obtain a third caprolactam crystal and a second crystallization mother liquor;

(6) subjecting the third caprolactam crystal to a second washing to obtain a fourth caprolactam and a second washing liquid;

(7) optionally concentrating the second crystallization mother liquor, then subjecting the concentrated second crystallization mother liquor to a thermostatic crystallization to obtain a third slurry, which is subjected to a third solid-liquid separation to obtain a fifth caprolactam crystal and a third crystallization mother liquor;

(8) subjecting the fifth caprolactam crystal to a third washing to obtain a sixth caprolactam crystal and a third washing liquid;

(9) subjecting the second caprolactam crystal obtained in step (3) to a hydrogenation reaction;

wherein the thermostatic crystallization is carried out in the presence of a thermostatic crystallization solvent comprising solvent A and ethanol, the solubility of caprolactam in solvent A at a temperature of 20° C. is less than 5 wt %, and ethanol is less than 2 wt % of the total amount of thermostatic crystallization solvent.

Preferably, the process further comprises recycling the fourth caprolactam crystal and the sixth caprolactam crystal to step (1) and blend with the crude caprolactam for carrying out the first evaporative crystallization.

Preferably, the crude caprolactam is obtained by subjecting the gas phase Beckmann rearrangement reaction product of cyclohexanone oxime to the solvent recovery, dehydration, and removal of light component.

Preferably, the solvent for the gas phase Beckmann rearrangement reaction of cyclohexanone oxime is ethanol.

In a second aspect, the present disclosure provides a refining system of caprolactam comprising a first evaporative crystallizer, a first solid-liquid separation device and a first washing device connected in series, wherein an outlet of the first evaporative crystallizer is in communication with an inlet of the first solid-liquid separation device, and the solid phase outlet of the first solid-liquid separation device is in communication with an inlet of the first washing device;

the system further comprises a second evaporative crystallizer, a second solid-liquid separation device and a second washing device successively connected in series, wherein an inlet of the second evaporative crystallizer is in communication with the liquid phase outlet of the first solid-liquid separation device, an outlet of the second evaporative crystallizer is in communication with an inlet of the second solid-liquid separation device, and a solid phase outlet of the second solid-liquid separation device is in communication with an inlet of the second washing device; optionally a first solvent recovery column is disposed at the communication pipeline between an inlet of the second evaporative crystallizer and the liquid phase outlet of the first solid-liquid separation device;

the system further comprises a thermostatic crystallizer, a third solid-liquid separation device and a third washing device connected in series, wherein an inlet of the thermostatic crystallizer is in communication with the liquid phase outlet of the second solid-liquid separation device, an outlet of the thermostatic crystallizer is in communication with an inlet of the third solid-liquid separation device, the solid phase outlet of the third solid-liquid separation device is in communication with an inlet of the third washing device; optionally a second solvent recovery column is arranged at the communication pipeline between an inlet of the thermostatic crystallizer and the liquid phase outlet of the second solid-liquid separation device;

the system further comprises a hydrogenation reactor, an inlet of the hydrogenation reactor is in communication with the solid phase outlet of the first washing device.

Preferably, the solid phase outlet of the second washing device and the solid phase outlet of the third washing devices are respectively in communication with an inlet of the first evaporative crystallizer.

The inventors of the present disclosure have discovered in the research process that, although caprolactam has a very high solubility in ethanol, both caprolactam and ethanol are in a mutually soluble state, the caprolactam crystal hardly precipitate from ethanol, so that ethanol cannot be used as a crystallization solvent for caprolactam under the normal condition, the inventors have found that the addition of a small amount (less than 2 wt %) of ethanol to the thermostatic crystallization solvent during a thermostatic crystallization process, in combination with the above specific solvent A and the specific refining method can make the impurities to be easily dissolved in the thermostatic crystallization solvent, so as to facilitate removal of impurities while having little influence on caprolactam yield, and it can advantageously improve caprolactam product quality, particularly having a significant effect on improving chroma of caprolactam; on the contrary, the caprolactam yield will decrease by 3-5% for each addition of 1 wt % of ethanol when the content of ethanol is more than 2 wt % of the thermostatic crystallization solvent; therefore, the added amount of ethanol is very important, the addition of more than 2 wt % of ethanol will seriously affect caprolactam product yield, such an addition becomes industrially impractical. As a result, a use of the specific refining process of the present disclosure can ensure caprolactam yield which is more than 99%, and can guarantee the excellent quality of caprolactam; in addition, the scale formation phenomenon in the crystallizer can be effectively alleviated due to the presence of ethanol having a modifier effect in the crystallization solvent.

The inventors have further discovered that the quality and yield of caprolactam can be further improved by using the crude caprolactam, which is obtained by subjecting the gas phase Beckmann rearrangement reaction product of cyclohexanone oxime to the solvent recovery, dehydration and removal of lighten components, as the raw material for the first evaporative crystallization.

Furthermore, the use of a preferred solution that the solvent for the gas phase Beckmann rearrangement reaction of cyclohexanone oxime is ethanol, it can reduce the amount and variety of impurities, and is more conducive to the refining and purification of caprolactam, further increases selectivity of caprolactam, and reduce variety and content of by-products, thereby further benefiting the improvement of the yield and quality of caprolactam. While in the prior art, the commonly used reaction solvent methanol also participates in side reactions to generate a variety of impurities, and some impurities have a low content, which brings difficulty for the separation of caprolactam from the impurities. Among the impurities, some impurities with a trace amount seriously affect the chroma, extinction value, volatile bases, and other quality indicators of the caprolactam product.

By means of the above refining system of the present disclosure, the aforementioned specific refining process can be performed, thereby obtaining the caprolactam with high yield and quality.

BRIEF DESCRITION OF THE DRAWINGS

The FIGURE illustrates a flow chart of the process of the present disclosure.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point values of the various ranges, and the individual point values may be combined with one another to produce one or more new numerical ranges, which should be deemed have been specifically disclosed herein.

As previously described, a first aspect of the present disclosure provides a process for refining caprolactam, wherein the process comprises the following steps:

(1) subjecting a crude caprolactam (i.e., crude CPL) having a caprolactam content not less than 98 wt % to a first evaporative crystallization in the presence of a first crystallization solvent, so as to obtain a first slurry;

(2) subjecting the first slurry to a first solid-liquid separation to obtain a first caprolactam crystal and a first crystallization mother liquor;

(3) subjecting the first caprolactam crystal to a first washing to obtain a second caprolactam crystal and a first washing liquid;

(4) optionally concentrating the first crystallization mother liquor and then subjecting the concentrated first crystallization mother liquor to a second evaporative crystallization to obtain a second slurry;

(5) subjecting the second slurry to a second solid-liquid separation to obtain a third caprolactam crystal and a second crystallization mother liquor;

(6) subjecting the third caprolactam crystal to a second washing to obtain a fourth caprolactam and a second washing liquid;

(7) optionally concentrating the second crystallization mother liquor, then subjecting the concentrated second crystallization mother liquor to a thermostatic crystallization to obtain a third slurry, which is subjected to a third solid-liquid separation to obtain a fifth caprolactam crystal and a third crystallization mother liquor;

(8) subjecting the fifth caprolactam crystal to a third washing to obtain a sixth caprolactam crystal and a third washing liquid;

(9) subjecting the second caprolactam crystal obtained in step (3) to a hydrogenation reaction;

wherein the thermostatic crystallization is carried out in the presence of a thermostatic crystallization solvent comprising solvent A and ethanol, the solubility of caprolactam in solvent A at a temperature of 20° C. is less than 5 wt %, and ethanol is less than 2 wt % of the total amount of thermostatic crystallization solvent.

The solid-liquid phase equilibrium relationship between a solid and a solution is usually expressed by the solubility of the solid in the solvent. In the present disclosure, the solubility refers to the amount of caprolactam in the solution at a specific temperature, when the solvent and caprolactam reach a (physical) solid-liquid phase equilibrium (i.e. a saturated solution is formed), the solubility can also be called as the dissolving capacity.

The inventors of the present disclosure have discovered in their researches that the ethanol contained in the thermostatic crystallization solvent can ensure removal of impurities, especially the colored impurities; in addition, the solvent A may guarantee the yield of caprolactam, and the use of ethanol solvent in combination with solvent A according to a specific weight ratio can produce a desirable refining effect, although the skilled person in the art will not consider the use of ethanol solvent and solvent A in combination because of the large dissolving capacity of ethanol and caproalctam, wherein ethanol ensures the purity, quality and chroma of the CPL product, and solvent A (which is inexpensive, readily available, and has high purity) guarantees the crystal form (i.e., morphology) and the yield of CPL. Preferably, the thermostatic crystallization solvent comprises ethanol in an amount of 2 wt % or less, and a solvent A in an amount of 98 wt % or more.

Preferably, ethanol is present in the thermostatic crystallization solvent in an amount of 0.5-2 wt %, more preferably 1-2 wt %, of the total amount of thermostatic crystallization solvent. A use of the preferred embodiment, it is advantageous to improve the yield and quality of caprolactam.

The present disclosure does not impose limitation on the mode of introducing the solvent A and ethanol of the thermostatic crystallization solvent, provided that the thermostatic crystallization is performed in the presence of the above thermostatic crystallization solvent; for example, the solvent A and ethanol can be introduced independently at least in part as the first crystallization solvent in step (1), or be introduced before or after the optionally concentrating process in step (4), or be introduced before or after the optionally concentrating process in step (7); the solvent A and ethanol can also be introduced independently at once or in batches at different steps for multiple times. Preferably, the solvent A and ethanol in the thermostatic crystallization solvent are introduced as at least a part of the first crystallization solvent, such that the first evaporative crystallization, the second evaporative crystallization, and the thermostatic crystallization are performed in the presence of ethanol, and it is more conducive to preventing occurrence of the oil precipitation phenomenon, and improving the product quality of caprolactam.

In the present disclosure, each of the first slurry, the second slurry, and the third slurry is a caprolactam-containing solution obtained under the respective and corresponding conditions.

In the present disclosure, in step (1), it is preferred that the skilled person in the art may refer to the practical requirement and arrange that the crude caprolactam is initially mixed with the first crystallization solvent and dissolved therein, and the first evaporative crystallization is performed after the crude caprolactam is completely dissolved in the first crystallization solvent, as shown in FIG. 1.

According to the present disclosure, the final temperature of the second evaporative crystallization may be identical with or different from the final temperature of the first evaporative crystallization; preferably, the second evaporative crystallization has an final temperature not higher than the final temperature of the first evaporative crystallization, more preferably, the second evaporative crystallization has a final temperature that is 5-20° C., more preferably 10-20°

C. lower than the final temperature of the first evaporative crystallization. The adoption of the preferred embodiment can further improve the caprolactam yield.

In the present disclosure, the final temperature refers to an end temperature at the termination of experiment of the first evaporative crystallization or the second evaporative crystallization.

In the present invention, the experiment is stopped after reaching the final temperature during the first evaporative crystallization or second evaporative crystallization process, and then generally, the skilled person can optionally retain the final temperature for a period of time according to practical requirements so that the crystallization process is more complete, the crystallization and dissolution processes are perfected, which is advantageous to further improve the crystal quality and the product yield; preferably, the residence time at the final temperature will be within a range of 30-100 min, more preferably 30-60 min.

In the present disclosure, it is preferable that, after complete dissolution of caprolactam in the corresponding crystallization solvent during the first evaporative crystallization or the second evaporative crystallization process, the process of cooling down to a final temperature may be carried out at once, or be carried out gradually for a plurality of stages, the latter is preferable, to finally reach a final temperature and stop the experiment, then the skilled person in the art may retain the final temperature for a certain time period depending on the practical requirements.

According to a preferred embodiment of the present disclosure, the first evaporative crystallization and the second evaporative crystallization are conducted under the vacuum conditions, which makes the apparatus to be simple and easy to operate, while in the prior art, a falling-down crystal under an atmospheric pressure and air-tight system (e.g., CN104024221A, CN104011017A) is used, it requires a cooling apparatus, and the upper part of the wall of the crystallizer is scarred due to splashing of the feedstock. In the present disclosure, vacuum degree refers to an absolute vacuum degree, which can be regulated by controlling the operating pressure.

Preferably, the vacuum degree of the second evaporative crystallization is not higher than that of the first evaporative crystallization. More preferably, the vacuum degree of the second evaporative crystallization is 5-20 kPa, more preferably 5-15 kPa lower than that of the first evaporative crystallization. In the present disclosure, the vacuum degree herein means the final vacuum degree, and the person skilled in the art can perform depressurization at one or stepwise in multiple stages depending on the practical requirements, during a depressurization process from the initial vacuum degree to the final vacuum degree, the latter is preferred.

It is preferable in the present disclosure that during the first evaporative crystallization or the second evaporative crystallization process, after caprolactam is completely dissolved in the corresponding crystallization solvent, the cooling process may be initially performed, followed by vacuumization and performing the corresponding evaporative crystallization, controlling the evaporation amount to uniformly evaporate the solvent, the temperature of the liquid phase in the crystallization vessel will decrease accordingly, then a stepwise cooling process is implemented, which is accompanied with a process of gradually decreasing the operating pressure (controlled by vacuumization), until the temperature of the solution in the crystallizer reaches the final temperature, stopping the experiment, and retaining the temperature for a certain time (i.e., holding time, preferably 30-100 min) to obtain the corresponding caprolactam crystal and alkane solution. The present disclosure does not impose limitation in regard to the magnitude of the stepwise cooling or depressurization, as long as it is advantageous to increase the yield and quality of caprolactam, and the present disclosure is not limited thereto. Typically, the operating pressure is determined depending on the saturated vapor pressure of the crystallization solvent. For instance, on condition that the crystallization solvent is pure isopropyl ether, the saturated vapor pressure at 50° C. is 387.6 mbar, and the operation shall be performed having an operating pressure above a saturated vapor pressure at 50° C. (e.g., 410 mbar, 460 mbar). Typically, the crystallization temperature and the operating pressure are arranged to match with each other, and the operating pressure shall be adjusted accordingly for each temperature decline of 3-5° C.

The conditions for the corresponding crystallization are not particularly limited in the present disclosure. Preferably, the temperature of the solution (i.e., the corresponding crystallization solvent) or melt during the crystallization is not higher than the melting point (70° C.) of caprolactam, and the temperature is preferably between −10° C. and the melting point of caprolactam, especially between 10° C. and the melting point of caprolactam.

According to the present disclosure, it is preferable that the conditions for the first evaporative crystallization comprise a final temperature within a range of 10-65° C., further preferably 30-60° C., more preferably 30-40° C.; and a vacuum degree of 5-80 kPa, further preferably 10-60 kPa, more preferably 20-30 kPa.

According to the present disclosure, it is preferable that the conditions for the second evaporative crystallization comprise a final temperature within a range of 5-60° C., further preferably 10-50° C., more preferably 15-25° C.; and a vacuum degree of 0-70 kPa, further preferably 5-50 kPa, more preferably 10-20 kPa.

In the step (1) or step (4) of the present disclosure, during the first evaporative crystallization or the second evaporative crystallization process, the solvent is continuously volatilized and decreased and the caprolactam precipitates in the solvent and constantly grows under the corresponding temperature and vacuum, thereby obtain a first slurry or a second slurry.

The used amount of the first crystallization solvent in present disclosure may be selected in a wide range, provided that it is conducive to improving the yield and quality of caprolactam. Preferably, the first crystallization solvent in step (1) is used in an amount that the solid content of caprolactam in a mixture of the crude caprolactam and the first crystallization solvent is 35 wt % or less, and further preferably 25-33 wt %.

According to the present disclosure, it is preferable that the first crystallization mother liquor in step (4) is subjected to concentrating, which causes that the obtained product has a solid content of caprolactam being 15 wt % or more, more preferably 18 wt % or more, most preferably 18-25 wt %.

The present disclosure does not impose limitation on the apparatus used for the first evaporative crystallization and the second evaporative crystallization, which may be a vacuum-insulated crystallizer or an insulated glass-crystallizing kettle, for example.

The first crystallization solvent of the present disclosure may be selected from a wide range, provided it is advantageous to improve caprolactam yield and quality, the category of the first crystallization solvent and the category of the thermostatic crystallization solvent may be identical or different. It is preferable that the first crystallization solvent comprises solvent A. A use of the preferred embodiment of the present disclosure can further improve caprolactam yield and ensure product quality.

According to the present disclosure, it is preferable that the first crystallization solvent comprises solvent A and further comprises ethanol, ethanol is 2 wt % or less, further preferably 0.5-2 wt %, more preferably 1-2 wt % of the total amount of the first crystallization solvent. In this preferred embodiment, the addition of ethanol can raise the crystallization temperature, inhibit and defer the oil precipitation phenomenon. While the method of the prior art lacks a step of adding ethanol, the oil precipitation phenomenon will easily occur, thus seriously affects the product quality of caprolactam, the reason is that a large amount of impurities will be enriched on caprolactam crystal if the crystallization is performed after the oil precipitation.

According to the present disclosure, it is preferable that the solvent A is at least one selected from the group consisting of halogenated hydrocarbons, ethers, and alkanes having 6-12 carbon atoms. The preferred embodiment can further improve the quality and yield of caprolactam. The inventors of the present disclosure have discovered that, although caprolactam has a small solubility in alkanes, it is possible to further improve the yield of caprolactam by using the preferred embodiment of the present disclosure, as the solvent A is inexpensive, safe and easily available, has a suitable boiling point, and recovering the solvent requires a low energy consumption.

In accordance with the present disclosure, it is preferable that the halogenated hydrocarbon is at least one selected from the group consisting of 1-chloropropane, 2-chloropropane, 1-chlorobutane, 2-chlorobutane, chloroisobutane, chloro-sec-butane, chloro-tert-butane, n-bromopropane, bromoisopropane, 1-bromobutane and 2-bromobutane.

According to the present disclosure, the ethers may be selected from a wide optional range, preferably the ethers are ethers having 2-6 carbon atoms, further preferably at least one selected from the group consisting of methyl ethyl ether, ethyl ether, n-propyl ether, isopropyl ether, n-butyl ether, ethyl ether, ethylene glycol dimethyl ether, vinyl ether, methyl t-butyl ether and ethyl t-butyl ether. Under the preferred embodiment, it is possible to further promote improvement of both the quality and yield of caprolactam.

More preferably, said ether is isopropyl ether. The inventors have further found that, under this preferred embodiment, isopropyl ether is particularly suitable as a caprolactam crystallization solvent, and especially suitable for use in an evaporative crystallization, because the isopropyl ether has a low boiling point, it can be easily recovered and recycled (simply by means of vacuumization) when it is used as a crystallization solvent, and the caprolactam product has an excellent quality, when combining it with the abovementioned specified methods of the first evaporative crystallization, the second evaporative crystallization, and the thermostatic crystallization, it can also ensure the caprolactam yield.

The present disclosure does not impose limitation to the kind of the alkane, which may be a straight-chain aliphatic hydrocarbon, a branched-chain aliphatic hydrocarbon, or a cyclic alkane; preferably, alkane having 6-12 carbon atoms is at least one selected from the group consisting of n-hexane, n-heptane, n-octane, n-nonane, methylhexane, isohexane, neohexane, isoheptane, isooctane, isononane, cyclohexane, methylcyclopentane and methylcyclohexane.

It is preferable that the boiling point of the alkane having 6-12 carbon atoms is within a range of 60-180° C., preferably 70-130° C.

According to the present disclosure, it is preferable that the solvent A is at least one selected from the group consisting of isopropyl ether, n-heptane, isooctane, chlorosec-butoxane and cyclohexane. By using the preferable embodiment, it is more advantageous to improve the quality and yield of caprolactam. Based on the preferable embodiment, the inventors of the present disclosure have further discovered that the solubility of caprolactam in n-heptane is particularly small, so that the crystallization yield is particularly high, but an oil precipitation phenomenon occurs when the corresponding crystallization process is carried out, it seriously affects the quality of caprolactam as a whole, and the solubility of impurities in n-heptane is also particularly small, thus its capability of removing impurities is not as strong as the isopropyl ether; given that the isopropyl ether has a low boiling point, strong volatility, a wide explosion range, a high content of saturated water, and high capacity of dissolving caprolactam and impurities, thus the finally produced product has better quality. The inventors have further found that a use of the mixture of isopropyl ether and n-heptane, or the mixture of isopropyl ether and ethanol can generate more desirable effects, which can ensure the product quality of caprolactam and the yield of caprolactam crystallization, and does not form an oil precipitation phenomenon.

In a preferred embodiment of the present disclosure, the first crystallization solvent is selected from the group consisting of ether and ethanol, and the thermostatic crystallization solvent comprises ether and ethanol. By using the preferred embodiment, it is possible to take full advantage of the corresponding crystallization solvent in regard to removing impurities, eliminating the colored substance, and improving chroma of caprolactam, thereby further enhancing caprolactam quality and yield. The inventors have further discovered that by using the preferred embodiment of the present disclosure, the addition of ethanol in a specific amount (less than 2 wt %) can take out the large amount of saturated water in the ether through an azeotropic distillation process, and preventing oil precipitation. While in the methods of the prior art, a high content of saturated water in the ether may cause a series of problems, such as the free water will occur in the crystallization system, which causes that the crystallization product yield is lower, and the product quality will deteriorate.

According to the present disclosure, it is preferable that the temperature of the first washing in step (3) is not lower than the final temperature of the first evaporative crystallization, and more preferably, the temperature of the first washing differs from the final temperature of the first evaporative crystallization by 0-2° C. The inventors have found that when the temperature of the first washing is higher than the final temperature of the first evaporative crystallization, there is some solvent in the caprolactam crystal; when the temperature of the first washing is not higher than the final temperature of the first evaporative crystallization, and crystals with a smaller particle size will precipitate.

In accordance with the present disclosure, the amount of washing solvent used in the first washing process may be selected from a wide range, provided it is advantageous to increase the yield of caprolactam; preferably, the weight ratio of the used amount of washing solvent in the first washing relative to the first caprolactam crystal is 0.5-1.5:1.

The present disclosure does not impose limitation on the kind of the washing solvent, as long as it fulfills the purpose of washing out impurities as much as possible; preferably, the washing solvent used in the first washing is identical with the first crystallization solvent. A use of the preferred embodiment may, on the one hand, facilitate storage and use of the solvent, and on the other hand, allow the washing solvent to be directly used as the crystallization solvent after being recovered.

According to the present disclosure, it is preferable that the temperature of the second washing in step (6) is not lower than the final temperature of the second evaporative crystallization, more preferably, the difference between the temperature of the second washing and the final temperature of the second evaporative crystallization is 0-2° C.

In accordance with the present disclosure, the amount of washing solvent used in the second washing may be selected from a wide range, provided it is conducive to improving the yield of caprolactam; preferably, the weight ratio of the used amount of washing solvent in the second washing relative to the third caprolactam crystal is 0.5-1.5:1.

According to the present disclosure, it is preferable that the temperature of the third washing in step (8) is not lower than the thermostatic crystallization, more preferably, the difference between the temperature of the third washing and the temperature of the thermostatic crystallization is 0-2° C.

Preferably, the weight ratio of the used amount of washing solvent in the third washing relative to the fifth caprolactam crystal is 0.5-1.5:1.

The present disclosure does not impose limitation on the kind of washing solvent used for the second washing and the third washing, provided the purpose of washing impurities as much as possible can be achieved; preferably, the washing solvents used in the second washing and the third washing are respectively and independently identical with the first crystallization solvent and/or the thermostatic crystallization solvent. The adoption of the preferred embodiment may, on the one hand, facilitate storage and use of the washing solvent in a simple, convenient, economically affordable manner, and on the other hand, have strong universality such that the recovered washing solvent can be directly used as the crystallization solvent.

It is preferable in the present disclosure that the process further comprises: recycling the first washing liquid to provide at least one of the following components: at least a portion of the first crystalline solvent, the second washing solvent used in the second washing, and the washing solvent used in the third washing. A use of the preferred embodiment can take full advantage of the characteristics that the first washing solution obtained by the first washing has a low content of impurities and a low content of caprolactam, thereby further improving utilization ratio of the solvent and saving the used amount of raw materials.

According to the present disclosure, it is preferable that the process further comprises: recycling the second washing liquid to provide at least a portion of the washing solvent used in the third washing.

According to the present disclosure, it is preferable that the process further includes: mixing the third washing liquid with the second crystallization mother liquor to jointly carry out the thermostatic crystallization. In this preferred embodiment, the caprolactam yield can be further increased.

In a preferred embodiment of the present disclosure, the temperature of said thermostatic crystallization in step (7) is lower than the final temperature of said second evaporative crystallization, preferably, the temperature of said thermostatic crystallization is lower than the final temperature of said second evaporative crystallization by 5-20° C. A use of the preferred embodiment of the present disclosure is more conducive to improving product quality and yield of caprolactam.

According to the present disclosure, if the caprolactam content of the third crystallization mother liquor is relatively high, the skilled person in the art may refer to the practical requirement, and carry out once more thermostatic crystallization in regard to the third crystallization mother liquor in step (7) in order to recover caprolactam from the third crystallization mother liquor as much as possible, or consider the measures such as the final temperature of the thermostatic crystallization in step (7) is adjusted to a lower temperature, the crystallization residence time is longer, so as to further recover caprolactam.

It is preferable that the conditions of thermostatic crystallization comprise a temperature within a range of 5-50° C., further preferably 10-40° C., more preferably 10-20° C. In the present disclosure, the skilled person in the art may refer to the practical requirements and adjust the operating pressure of the thermostatic crystallization, the crystallization temperature and operating pressure are generally arranged in a matching manner, and the present disclosure is not limited thereto. During the thermostatic crystallization process of the present disclosure, the skilled person in the art may optionally lengthen the residence time of the thermostatic crystallization according to practical requirements, in order to ensure the large crystal particles to facilitate separation, and the present disclosure is not limited thereto. Preferably, the residence time (i.e., holding time) is within a range of 20-45 min.

In the present disclosure, the concentration is preferably performed in the step (4) and the step (7), and the present disclosure does not impose limitation on the concentration mode and the equipment used for concentration, both can be freely selected by the skilled person in the art according to the practical requirements, for example, the concentration may be carried out in a solvent recovery column by means of distillation or evaporation. The present disclosure does not limit the conditions of concentration (i.e., solvent recovery), the skilled person in the art may voluntarily choose the conditions according to actual demand, provided it is conducive to the concentration and the solvent recovery; for example, when the first crystallization solvent is isopropyl ether, the first solvent recovery column (i.e., concentration column) may be the isopropyl ether solvent recovery column, the pressure at tower top is atmospheric, the temperature at tower top is 70° C., the tower kettle temperature is 90° C., the feedstock temperature is 71° C., and the second solvent recovery column may be the de-etherization column, the pressure at tower top is atmospheric, the temperature at tower top is 84-90° C., the tower kettle temperature is 100-105° C. As for the other crystallization solvents and washing solvents, each is operated under an atmospheric pressure, but the other conditions are different according to the various boiling points thereof.

It is preferable that the second crystallization mother liquor in step (7) is subjected to concentrating, which causes that the obtained product has a solid content of caprolactam within a range of 15-30 wt %. In step (7) of the present disclosure, ethanol can be added or not added prior to the concentration process according to the practical requirements, provided it meets the aforementioned requirements that the solid content of caprolactamis within the range of 15-30 wt %, and the thermostatic crystallization is performed in the presence of a thermostatic crystallization solvent containing a specified content of ethanol.

The present disclosure does not impose limitation on the equipment used for the thermostatic crystallization, it can be voluntarily selected by the skilled person in the art according to practical requirements, and for example, it may be a thermostatic crystallizer.

The skilled person in the art may refer to the practical requirements and voluntarily choose to add the seed crystal or not during the first evaporative crystallization, the second evaporative crystallization or the thermostatic crystallization, which is not limited in the present disclosure.

In the present disclosure, the skilled person in the art may refer to the practical requirements and carry out the corresponding crystallization step for once or several times (for example, the first evaporative crystallization process is continuously performed for several times or once). However, according to the method provided by the present disclosure, the favorable effects can be produced by means of performing the corresponding crystallization operation for once, thus it is preferable to adopt the corresponding crystallization process for once.

In step (2), step (5) or step (7) of the present disclosure, since a portion of the residual solvent is also disposed on the surface of the corresponding caprolactam crystal obtained after the corresponding solid-liquid separation, the skilled person in the art may optionally recover the solvent by a stripping process as required.

In the present disclosure, the first washing, the second washing and the third washing are carried out by the skilled person in the art accordingly for one or more times, depending on practical requirements. In the present disclosure, during the first washing, the second washing and the third washing process, the skilled person in the art can carry out solid-liquid separation in regard to the washed mixture materials by using any conventional and existing solid-liquid separation method, so as to obtain the corresponding caprolactam and the corresponding washing liquid; for example, as shown in FIG. 1, the first washing in step (3) is followed by a solid-liquid separation to obtain the second caprolactam crystal and the first washing liquid.

In the present disclosure, each of the first solid-liquid separation of step (2) and the first washing and the corresponding solid-liquid separation after the first washing of step (3), the second solid-liquid separation of step (5) and the second washing and the corresponding solid-liquid separation after the second washing of step (6), and the third solid-liquid separation of step (7) and the third washing and the corresponding solid-liquid separation after the third washing of step (8) can be performed respectively and independently by two equipment (e.g., on a washing tank and a centrifuge) separately, or be performed simultaneously by an equipment (e.g., a filter press or a counter-current washing apparatus) by means of a counter-current washing, the present disclosure is not limited thereto; preferably, the filter press equipment having both the solid-liquid separation and the washing functions is used.

The present disclosure does not impose limitation on the solid-liquid separation mode, which may be any solid-liquid separation mode in the prior art, such as a centrifugal separation or a filtration separation, wherein the centrifugal separation process may be performed by using a pushrod centrifuge, which may operate in one or more steps, or a sieve plate convey centrifugal machine or a spiral convey centrifugal machine (decanter); the filtering process may be implemented by a suction filter (which may operate batch-wise or continuously, optionally mounted with a stirrer) or a belt filter.

The hydrogenation reaction in step (9) of the present disclosure may be selected from a wide range, and it is preferable that the hydrogenation reaction in step (9) is performed in the presence of water and a hydrogenation catalyst.

As shown in FIG. 1, it is preferable in the present disclosure that the step (9) comprises initially dissolving the second caprolactam crystal with water (or water and a hydrogenation catalyst), subsequently performing the hydrogenation reaction.

According to the present disclosure, during the hydrogenation reaction process, it is preferable that the used amount of water is 10-200 parts by weight, more preferably 10-40 parts by weight, relative to 100 parts by weight of the second caprolactam crystal. A use of the preferred solution is conducive to reducing the waste water discharge and improving yield, and saving energy as well; while in the prior art, which uses 30 wt % of caprolactam and 70 wt % of water, discharges a large amount of waste water, has a large energy consumption, and is prone to cause loss of caprolactam.

The present disclosure does not limit the kind of the hydrogenation catalyst as long as hydrogenation of impurities in the third caprolactam crystal can be achieved; preferably, the hydrogenation catalyst is at least one selected from the group consisting of a nickel based catalyst, a palladium based catalyst, and a platinum based catalyst, more preferably a nickel-based catalyst. The nickel-based catalyst is further preferably an amorphous nickel catalyst.

The present disclosure does not impose limitation on the conditions of the hydrogenation reaction, which may be the existing hydrogenation conditions in the art, and can be voluntarily selected by those skilled in the art according to practical requirements; preferably, the conditions of hydrogenation reaction comprises a temperature of 50-150° C., a pressure of 0.2-2 MPa, and the hydrogen is used in an amount of 0.01-0.25 mole relative to 1 mole of the second caprolactam crystal. In the hydrogenation reaction of the present disclosure, unreacted hydrogen can be recycled. In the present disclosure, the pressure refers to an absolute pressure unless otherwise specified.

According to the present disclosure, the hydrogenation reaction can be either a batch operation or a continuous operation. The present disclosure does not impose limitation to the used amount of the hydrogenation catalyst, which may be an amount in the prior art, and can be voluntarily selected by the skilled person in the art according to practical requirements. When the hydrogenation reaction is a batch operation, the hydrogenation reaction time may be within a range of 0.5-3 hours, more preferably 1-2 hours; the used amount of the hydrogenation catalyst is 0.001-0.02 parts by weight, more preferably 0.003-0.01 parts by weight, relative to 100 parts by weight of the third caprolactam crystal; whereas the concentration of the hydrogenation catalyst in the conventional large-scale industry facility is about 50-100 μg/g, and the used amount of the hydrogenation catalyst in the present disclosure can ensure the hydrogenation effect, and the used amount of the hydrogenation catalyst is generally scaled up in an equal proportion to the caprolactam content. When the hydrogenation reaction is a continuous operation (e.g., fixed-bed process), the weight hourly space velocity of caprolactam can be 0.5-30 $h^{-1}$.

The present disclosure does not impose specific limitation on a reactor for carrying out said hydrogenation reaction, the reactor can be voluntarily selected by the skilled person in the art as required, for example, the reactor may be a magnetically stable bed reactor, a fixed bed reactor or a slurry bed reactor, preferably a slurry bed reactor, wherein the hydrogenation reaction of caprolactam in a molten state or caprolactam in an aqueous solution may be performed by selecting a fixed bed reactor.

In the present disclosure, after the hydrogenation reaction is carried out, the skilled person in the art can subject the product obtained from the hydrogenation reaction to the evaporation, dehydration and distillation process to obtain a caprolactam product according to practical requirements. The present disclosure does not impose limitation to the evaporation, dehydration and distillation mode, provided that it is conducive to producing the caprolactam product with high quality and yield; preferably, the evaporation, dehydration and distillation comprises evaporative dehydration, triple effect evaporation, and distillation to finally obtain caprolactam with higher quality; the conditions for evaporative dehydration can be freely selected by the skilled person in the art according to practical requirements, the present disclosure does not impose limitation thereto. The present disclosure does not limit the apparatus for evaporation, dehydration and distillation, provided it is conducive to producing the caprolactam product with high quality and yield; for example, the apparatus may be a rotary evaporator.

In the present disclosure, performing the hydrogenation reaction of step (9) may, on the one hand, convert tetrahydro-azepin-2-one and isomers thereof, which are difficult to sufficiently remove by the crystallization process, into caprolactam, thereby further improving the purity of the finally produced caprolactam; on the other hand, effectively improve the potassium permanganate absorption value of the caprolactam product.

In order to further increase the yield of caprolactam, it is preferable that the process further comprises recycling the fourth caprolactam and the sixth caprolactam crystal to step (1) in admixture with the crude caprolactam to perform the first evaporative crystallization.

According to the present disclosure, it is preferable that the process further comprises: recovering solvent from the third crystallization mother liquor. The present disclosure does not impose limitation to the recovery method as long as the solvent recovery can be achieved; for example, the recovering process may be performed by using a recovery column, the solvent is recovered from a tower top outlet of the recovery column, and the heavy component residue is recovered at an outlet of the tower kettle, which can be discharged or incinerated by the skilled person in the art according to practical requirements.

In a preferred embodiment of the present disclosure, the crude caprolactam is obtained from the gas phase Beckmann rearrangement reaction product of cyclohexanone oxime through the steps of solvent recovery, dehydration and removing the light component. With this preferred embodiment, given that the crude caprolactam obtained from the gas phase Beckmann rearrangement reaction product of cyclohexanone oxime through the steps of solvent recovery, dehydration and removing the light component is used as the feedstock of the first crystallization, the heavy components are not removed. Although the feedstock is poor, it contains a relatively large amount of nitrogen-containing compound, particularly the chroma-affecting compounds, the inventors have discovered that the addition of ethanol in the above specified amount during the crystallization process can facilitate removal of the by-products and further improve the quality and yield of caprolactam. While in the prior art, the crude caprolactam after removing the heavy components is generally used as the feedstock of crystallization, the caprolactam produced with the method has a relatively low yield and quality and suffers from high energy consumption.

The present disclosure does not impose limitation on the method and apparatus for solvent recovery, dehydration and removing the light component, which may be the existing method and apparatus used in the art, provided it fulfills the corresponding purpose; for example, the apparatus may be a rotary evaporator, a dehydration column and a column for removing the light component, wherein the crude caprolactam is derived from a tower kettle of the column for removing the light component, and the light component is derived form a tower top of the column for removing the light component. The present disclosure does not impose limitation to the conditions of the dehydration column and the column for removing the light component, so long as it is conducive to dehydration and removing the light component; it is preferable that the conditions of the dehydration column comprise: a pressure of tower top within a range of 4-40 kPa, more preferably 10-40 kPa, further preferably 15-25 kPa; a tower top temperature within a range of 70-100° C., more preferably 70-75° C., a total reflux at the tower top, a tower kettle temperature within a range of 130-135° C., and a water content in the tower kettle less than 1 wt %. Preferably, the conditions of the column for removing the light component comprise: a tower top temperature within a range of 80-85° C., a column kettle temperature within a range of 145-150° C., a pressure of tower top within a range of 1-2 kPa, a tower top reflux ratio of 1:10-30, and a content of light component in the tower kettle being less than 0.2 wt %.

The present disclosure has no limitation on the conditions of the gas phase Beckmann rearrangement reaction, as long as it is conducive to increasing the yield and quality of caprolactam; preferably, the gas phase Beckmann rearrangement reaction is carried out in the presence of a molecular sieve catalyst with a MFI structure.

It is preferable in the present disclosure that the molecular sieve catalyst with a MFI structure contains a silica molecular sieve having MFI topology and a binder; the content of the molecular sieve based on the dry weight in the catalyst is 50-95 wt %, and the content of the binder in terms of oxide is 5-50 wt %, based on the dry weight of the catalyst;

the molecular sieve comprise metallic element, the ions of the metallic element have a Lewis acid characteristic; the content of the metallic element in the molecular sieve is 5-100 µg/g based on the total amount of the molecular sieve.

In the present disclosure, the term "the ions of the metallic element have a Lewis acid characteristic" means that the ions of the metal element can accept an electron pair.

It should be noted that the silica molecular sieve having a MFI topological structure of the present disclosure has an extremely small amount of metallic elements, and it is concluded that the small amount of metallic elements is present in the framework of the molecular sieve in the form of metal ions.

Preferably, in the silicon molecular sieve having a MFI topological structure according to the present disclosure, the metallic elements are present on the molecular sieve framework in the form of metal cations.

In the present disclosure, the content of the metallic element is measured by using an inductively coupled plasma (ICP) atomic emission spectrometer 7000DV, manufactured by PE (Perkin Elmer Incorporation) of the USA, under the test conditions as follows: the molecular sieve is dissolved by using HF acid or aqua regia to completely dissolve silicon oxide and metal oxide in the sample, and the content of metal ions is measured in an aqueous solution.

The present disclosure has wider selection range in regard to the contents of silicon element and oxygen element in the molecular sieve, and in a specific embodiment, the sum of the contents of the silicon element, the oxygen element and the metallic element in the molecular sieve is 100% based on the total amount of the molecular sieve.

According to a preferred embodiment of the present disclosure, the content of the metallic element in the molecular sieve is within a range of 6-90 µg/g, preferably 30-80 µg/g, based on the total amount of the molecular sieve. Specifically, the concentration may be for example 30 µg/g, 35 µg/g, 40 µg/g, 45 µg/g, 50 µg/g, 55 µg/g, 60 µg/g, 70 µg/g, 75 µg/g, 80 µg/g, or any value in the ranges formed by any two of the numerical values. In the preferred embodiment, the molecular sieve has better catalytic performance, and is more conducive to improving the conversion rate of cyclohexanone oxime and the selectivity of caprolactam. If the content of the metallic element in the present disclosure is excessive, the Lewis acid characteristic of the molecular sieve may be enhanced, which will induce the unnecessary side reactions, hamper improvement of the caprolactam selectivity; if the content of the metallic element is deficient, it is not beneficial to prolonging the service life of the molecular sieve catalyst and enhancing the stability.

Any metallic element whose ion has a Lewis acid characteristic may be used in the present disclosure, and preferably, the metallic element is at least one selected from the group consisting of transition metallic element, group IIIA element and group IVA element. Preferably, the transition metal element is at least one selected from the group consisting of group IB, group IIB, group IVB, group VB, group VIB, group VIIB and group VIII metal elements.

According to a preferred embodiment of the present disclosure, the metallic element is at least one element selected from the group consisting of Al, Ga, Ge, Ce, Ag, Co, Ni, Cu, Zn, Mn, Pd, Pt, Cr, Fe, Au, Ru, Rh, Ti, Zr, V, Mo and W.

Further preferably, the metallic element has an ionic valence state of +3 and/or an ionic valence state +4. The inventors of the present disclosure have discovered in the research process that the metallic element with an ionic valence state of +3 and/or an ionic valence state of +4 is more favorable for the metallic element to enter the molecular sieve skeleton and more conducive to charge balance.

According to the present disclosure, the metallic element is further preferably at least one element selected from the group consisting of Fe, Al, Ga, Ge, Cr, Ti, Zr, and Ce. Such a preferred embodiment is more beneficial to improve the performance of the molecular sieve, thereby improving the conversion rate of cyclohexanone oxime and the selectivity of caprolactam.

In accordance with a preferred embodiment of the present disclosure, the binder is silicon oxide.

The present disclosure provides a wide range of choices in regard to the preparation method, particle size, shape and loading amount of the catalyst, the skilled person in the art can appropriately select the specific reactor for the gas-phase Beckmann rearrangement reaction of cyclohexanone oxime. For example, the gas-phase Beckmann rearrangement reaction of cyclohexanone oxime may be performed in any one reactor selected from the group consisting of a fixed bed reactor, a radial flow moving bed reactor, a single-stage and multi-stage fluidized bed reactor, a reactor having a fluidized bed in combination with a fixed bed, and a reactor having a fluidized bed in combination with a moving bed. Preferably, the gas-phase Beckmann rearrangement reaction of cyclohexanone oxime is carried out in a fixed bed reactor, and the catalyst is in the form of a strip type (it can be obtained by extrusion molding) or a spherical shape (it can be obtained by rotational molding) with a diameter of 1-3 mm. Preferably, the gas-phase Beckmann rearrangement reaction of cyclohexanone oxime is carried out in a moving bed reactor, the catalyst is in the form of a spherical shape, and the catalyst has a particle size of 0.5-3 mm, preferably 0.8-2.5 mm (it can be obtained by rotational molding). Preferably, the gas-phase Beckmann rearrangement reaction of cyclohexanone oxime is implemented in a fluidized bed reactor, the catalyst is in the form of a spherical shape, and the catalyst has a particle size of 20-200 µm, preferably 40-150 µm (it can be obtained by mist spray forming). The present disclosure does not particularly limit the loading amount of the catalyst and the shape of the loaded catalyst in each reactor, and the shape of the loaded catalyst can be appropriately selected according to the variety of the reactor.

The present disclosure does not impose limitation to the preparation method of the catalyst used for carrying out the gas phase Beckmann rearrangement reaction, as long as the specific catalyst described before can be prepared. In a preferred embodiment of the present disclosure, the catalyst in use is obtained through mist spray forming, specifically, the preparation method of the catalyst comprises the following steps:

(a-1) mixing ethyl orthosilicate, ethanol, metal source, tetrapropylammonium hydroxide with water to obtain a colloid mixture; wherein the molar ratio of ethyl orthosilicate calculated by $SiO_2$, ethanol, tetrapropylammonium hydroxide and water is 1:(4-25):(0.06-0.45):(6-100); the weight ratio of the ethyl orthosilicate calculated by $SiO_2$ relative to the metal source calculated by metallic element is (10,000-200,000):1;

(a-2) subjecting the colloid mixture to a two-stage crystallization with an ethanol-hydrothermal system under variable temperatures, wherein the conditions of the two-stage crystallization with an ethanol-hydrothermal system under variable temperatures comprise: crystallizing at 40-78° C. for 0.5-5 days, and then crystallizing at 80-130° C. for 0.5-5 days;

(a-3) concentrating the crystallization mother liquor obtained in the step (a-2) to obtain a molecular sieve slurry;

(a-4) blending the molecular sieve slurry with a binder and pulping to obtain a molecular sieve-binder slurry; subjecting the molecular sieve-binder slurry to a mist spray forming, and then roasting;

(a-5) contacting the roasted product of step (a-4) with an alkaline buffer solution of a nitrogen-containing compound, and subsequently carrying out drying.

The ions of the metallic element in the metal source have a Lewis acid characteristic.

Unless otherwise specified in the present disclosure, the molar ratio and the mass ratio of the materials in the molecular sieve preparation process refer to the molar ratio and the mass ratio of the used amount when the materials are fed (charged).

According to a preferred embodiment of the present disclosure, the method for preparing the molecular sieve provided by the present disclosure does not include an addition of an organic amine. In this preferred embodiment, the molecular sieve has better properties. In the present disclosure, tetrapropylammonium hydroxide is used as an organic alkali and can also be used as a template agent, and an addition of the organic amine is not required. In the present disclosure, the organic amine refers to at least one of aliphatic amine compounds, and may be, for example, at least one of mono-n-propylamine, di-n-propylamine, tri-n-propylamine, ethylamine, n-butylamine, ethylenediamine and hexamethylenediamine.

According to the present disclosure, a specific silicon source, a specific metal source and a specific organic template agent are adopted in combination with ethanol, so as to prepare the molecular sieve with a specific structure under the condition of specific dosage, the molecular sieve has better catalytic performance. The molecular sieve is particularly suitable for gas phase Beckmann rearrangement reaction of cyclohexanone oxime, and is more favorable for improving the economic efficiency of the whole process.

According to a preferred embodiment of the present disclosure, the molar ratio of ethyl orthosilicate calculated by $SiO_2$, ethanol, tetrapropylammonium hydroxide and water is 1:(4-15):(0.06-0.3):(15-50), more preferably 1:(6-14):(0.1-0.25):(20-40). In this preferred embodiment, the produced molecular sieve has better catalytic performance.

According to a preferred embodiment of the present disclosure, the weight ratio of the ethyl orthosilicate calculated by $SiO_2$ relative to the metal source calculated by metallic element is (10,000-100,000):1, more preferably (15,000-50,000):1. Under the preferred embodiment, the more suitable amount of metal enters the skeleton of the molecular sieve, and it is more conducive to improving the catalytic performance of the molecular sieve.

According to the method provided by the present disclosure, the selection of the metallic element in the metal source is as previously mentioned, and the content is not repeated here.

The present disclosure has a wide range of choices for the metal source, which is a compound containing various metallic element and being capable of providing the metallic element, and the compound containing the metallic element is preferably soluble. In the present disclosure, the term "soluble" means that it can be dissolved in a solvent directly or in the presence of a co-solvent, and the solvent is preferably water.

According to the present disclosure, the metal source is preferably at least one selected from the group consisting of a metal nitrate, a metal chloride, a metal sulfate, a metal acetate, and an ester metal compound. In a specific embodiment, the ester metal compound is tetraethyl titanate and/or tetrabutyl titanate.

It is preferable in the present disclosure, when the metal is an Al element, the metallic aluminum source can also be a compound existing in the form of alumina, such as SB powder, V250 and pseudoboehmite According to a preferred embodiment of the present disclosure, the metal source is preferably at least one selected from the group consisting of $Fe(NO_3)_3$, $Ni(NO_3)_2$, tetrabutyl titanate, $Pd(NO_3)_2$, $Ce(NO_3)_4$, $Al(NO_3)_3$, $Cu(NO_3)_2$, $ZrOCl_2$, $Ga(NO_3)_3$, $H_2PtCl_6$ and $Cr(NO_3)_3$, and is further preferably at least one selected from the group consisting of $Fe(NO_3)_3$, tetrabutyl titanate, $Al(NO_3)_3$, $Ga(NO_3)_3$ and $Cr(NO_3)_3$. The metal source may either contain or not contain crystal water, and the present disclosure does not impose a particular limitation thereto.

The order of mixing in step (a-1) is not particularly limited in the present disclosure, as long as the colloidal mixture can be obtained; any two of the compounds may be initially blended and then mixed with the remaining substances, or any three of the compounds may be initially blended and subsequently mixed with the remaining substances. Preferably, it is desirable to avoid gel formation during the process of charging materials and also to prevent excessive temperature rise of the liquid phase during the process of charging materials.

According to the present disclosure, it is preferable that the mixing of step (a-1) comprises: blending ethanol and tetrapropylammonium hydroxide, then adding ethyl orthosilicate, and further adding water and a metal source.

The present application has wide selection ranges in regard to the specific operation of the mixing process, according to a preferred embodiment of the present disclosure, and the mixing is performed under the stirring conditions. In the present disclosure, the stirring time is not particularly limited, so long as the colloidal mixture can be obtained. For example, the mixture may be stirred at normal temperature (25° C.) for 2-6 hours.

According to a preferred embodiment of the present disclosure, the conditions of the two-stage crystallization with an ethanol-hydrothermal system under variable temperatures comprise: crystallizing at 50-80° C. for 1-1.5 days, and then crystallizing at 100-120° C. for 1-3 days. Under the preferred embodiment, the utilization rate of crystallization raw materials is further improved, and the prepared catalyst containing the molecular sieve has better catalytic performance under the specific crystallization conditions. In the present disclosure, the two-stage crystallization with an ethanol-hydrothermal system under variable temperatures is preferably performed in a closed system under an autogenous pressure, for example, in an airtight reaction kettle.

According to the present disclosure, it is preferable that the pH of the crystallization mother liquor is greater than 11, preferably not less than 13, such as 13-14.

In the present disclosure, the crystallization with an ethanol-water system means that the crystallization is performed under a saturated vapor pressure of a specific temperature in the co-presence of ethanol and water.

The present disclosure has a wide selection range in regard to the concentration mode in step (a-3), provides it can fulfill the purpose of increasing the solid content in the molecular sieve slurry.

It is preferable in the present disclosure that before the concentrating process, step (a-3) further comprises: washing the crystallization mother liquor until the pH of the wash water for washing the crystallization product is below 9.4, preferably below 9.2, for example, the pH is within a range of 8.5-9.2. The present disclosure does not impose specific limitation in regard to the washing process, which may be any of various washing methods conventionally used in the art; in addition, the detergent used in the washing process is not particularly limited in the present disclosure, it may be water, for example.

According to a preferred embodiment of the present disclosure, the crystallization mother liquor is washed with water at a temperature of 20-80° C.

According to a preferred embodiment of the present disclosure, the washing and concentration of the molecular sieve is carried out by means of membrane filtration, for example, by using a six-tube membrane. The specific operation is well-known among those skilled in the art, and the content will not be repeated here.

According to the process provided by the present disclosure, it is preferable that the process further comprises: the crystallization mother liquor is subjected to ethanol removal prior to the concentrating process (preferably prior to washing, if a washing process is also included in the process) in step (a-3). In the present disclosure, given that the ethanol contains organic oxygen during the industrial production, the discharge of ethanol into the sewage water may result in environmental problems, thus the ethanol removal operation is required.

The present disclosure has a wide selection range in regard to the conditions of ethanol removal, as long as the purpose of removing ethanol is achieved; the conditions of ethanol removal preferably comprise: the temperature is within a range of 50-90° C., preferably 60-90° C.; the time is within a range of 1-24 h, preferably 1-12 h. Specifically, the reaction kettle may be opened after the temperature of the reaction kettle is lowered to an operable temperature, and the temperature of the reaction kettle is then raised to 50-90° C. to evaporate ethanol. In the ethanol removal operation of the present disclosure, water can be added into the reaction kettle to maintain the liquid level of the reaction kettle, which is beneficial to improving efficiency of the ethanol removal process.

In the present disclosure, the solid content of the molecular sieve slurry is selected from a wide range, and preferably, the solid content of the molecular sieve slurry in step (a-3) is within a range of 15-60 wt %, preferably 20-50 wt %. The preferred embodiment is more conducive to improving performance of the prepared catalyst.

According to the present disclosure, the molecular sieve-binder slurry in step (a-4) preferably has a solid content of 10-40 wt %, preferably 10-35 wt %. It is more advantageous to carry out the mist spray forming under the preferred circumstance, such that the abrasion index of the catalyst is lower.

According to the present disclosure, it is preferable in the molecular sieve-binder slurry, the weight ratio of the molecular sieve based on the dry weight relative to the binder calculated by $SiO_2$ is 1:(0.05-1), preferably 1:(0.4-0.8), further preferably 1:(0.55-0.7). In the preferable embodiment, the catalyst has better performance, and it is more conducive to improving the conversion rate of cyclohexanone oxime and the selectivity of caprolactam.

According to the process provided by the present disclosure, it is preferable that the binder is a precursor of silicon oxide. The present disclosure provides a wide selection range for the precursor of the silicon oxide, as long as the precursor can be converted into the silicon oxide through the subsequent roasting process. Preferably, the precursor of the silicon oxide is silica sol and/or white carbon black, and further preferably silica sol. The silica sol and the white carbon black of the present disclosure are commercially available.

According to the present disclosure, the silica sol preferably has a $SiO_2$ content of 20-45 wt %, preferably 30-40 wt %.

According to the present disclosure, the silica sol may further contain sodium ions, the content of sodium ions is selected from a wide range of the present disclosure, and preferably, the content of sodium ions is not higher than 1,000 μg/g. In the preferred embodiment, it is more conducive to improving performance of the catalyst.

The mist spray forming of the present disclosure has the conventional meaning in the art. The conditions of the mist spray forming preferably cause that the particles obtained by the mist spray forming have a particle size of 20-200 μm, further preferably 40-150 μm.

According to the present disclosure, the conditions of the mist spray forming comprise: the inlet temperature is within a range of 200-300° C., preferably 250-280° C.; the outlet temperature is within a range of 100-150° C., and preferably 120-140° C. In the preferred embodiment, the catalyst has desirable performance, and it is more conducive to improving the conversion rate of cyclohexanone oxime and the selectivity of caprolactam.

According to the present disclosure, the roasting conditions preferably comprise: the temperature within a range of 200-600° C., preferably 250-550° C., and the time within a range of 1-20 h, preferably 2-18 h.

According to the present disclosure, it is preferable that the roasting may be a multi-stage roasting, and for instance, the roasting may specifically include stage 1) and stage 2); the conditions of the phase 1) comprise: a temperature within a range of 200-400° C., and the time within a range of 2-10 h; the conditions of the stage 2) comprise: a temperature within a range of 400-600° C., and the time within a range of 2-15 h.

According to a preferred embodiment of the present disclosure, the alkaline buffer solution of a nitrogen-containing compound comprises an ammonium salt and an alkali.

The solvent of the alkaline buffer solution of a nitrogen-containing compound may be selected from a wide range, the solvent is preferably water.

In the present disclosure, the ammonium salt is preferably ammonium nitrate and/or ammonium acetate.

According to the present disclosure, the alkali is preferably at least one selected from the group consisting of ammonia water, tetramethylammonium hydroxide, tetraethylammonium hydroxide and tetrapropylammonium hydroxide, more preferably ammonia water.

According to a preferred embodiment of the present disclosure, the ammonium salt is contained in an amount of 0.1-20 wt %, preferably 0.5-15 wt %; the alkali is contained in an amount of 5-30 wt %, preferably 10-28 wt %.

According to the present disclosure, it is preferable that the alkaline buffer solution of a nitrogen-containing compound has a pH within a range of 8.5-13.5, more preferably 10-12, and further preferably 11-11.5.

The present disclosure has wide selection range of the dosage of the alkaline buffer solution of a nitrogen-containing compound, it is preferable that the alkaline buffer solution of a nitrogen-containing compound is used in an amount of 500-1,500 parts by weight, more preferably 700-1,200 parts by weight, relative to 100 parts by weight of the roasted product on a dry basis.

According to the present disclosure, it is preferable that the contacting conditions comprise: a temperature within a range of 50-120° C., preferably 70-100° C.; a pressure within a range of 0.5-10 kg/cm$^2$, preferably 1.5-4 kg/cm$^2$; the time within a range of 0.1-5 h, preferably 1-3 h. In the present disclosure, the contacting process is preferably performed under the stirring conditions. The stirring speed is not particularly limited in the present disclosure, and it may be appropriately selected by those skilled in the art according to the actual situation.

According to the method provided by the present disclosure, the contacting process may be subjected to repetitive operation. The number of repetitions is not particularly limited in the present disclosure, it may be determined according to the effect of the contacting process; in order to improve the performance of the catalyst, for example, the contacting process may be repeated for 1-3 times.

The present disclosure does not impose specific definition in regard to the conditions for drying the product prepared by contacting the product obtained from the roasting process with the alkaline buffer solution of a nitrogen-containing compound, the drying process may be performed with any existing means in the prior art, as long as the solvent is removed, and the drying method includes, but is not limited to, natural drying, heat drying, and forced air drying, and specifically, for example, the drying temperature may be within a range of 100-120° C., and the drying time may be within a range of 2-36 hours.

According to the present disclosure, it is preferable that step (a-5) may further comprise: prior to the drying process, sequentially filtering and washing the substances obtained after the roasted product obtained in step (a-4) is contacted with the alkaline buffer solution of a nitrogen-containing compound. The detergent used in the washing process of the present disclosure is not particularly limited, for example, the detergent may be water. Specifically, the washing process may include: washing until the pH of the filtration clear solution is within a range of 9-10.5.

According to the present disclosure, the skilled person in the art may freely select the particle size and preparation method of the catalyst according to the type of the reactor, for example, it is preferable that the catalyst can be formed by rotary forming to obtain a catalyst having a particle diameter of mm order when the reaction is carried out in a moving bed reactor, the production method can comprise: filtering and drying the crystallization mother liquor from step (a-2) in sequence after performing the step (a-1) and step (a-2) mentioned above, so as to obtain a molecular sieve raw powder; pulverizing the molecular sieve raw powder and mixing the pulverized molecular sieve raw powder with a binder, and subsequently performing the rotary forming to obtain spherical particles; roasting the spherical particles, and then contacting the roasted spherical particles with an alkaline buffer solution of a nitrogen-containing compound, a drying process is then carried out. The conditions in the production method can be referred to conventional conditions in the art, and the present disclosure is not limited thereto.

The inventors of the present disclosure have discovered in the research process that the use of the above-mentioned catalyst with a specific structure in the aforementioned specific process can improve the selectivity of caprolactam and the conversion rate of cyclohexanone oxime.

The present disclosure does not impose limitation on the conditions of the gas phase Beckmann rearrangement reaction, as long as it is conducive to improving the yield and quality of caprolactam. Preferably, the conditions of the gas phase Beckmann rearrangement reaction comprise a temperature of 320-450° C. and a pressure of 0.05-0.5 MPa. Preferably, ethanol is used as the reaction solvent, and the weight hourly space velocity of cyclohexanone oxime is not more than 10 $h^{-1}$, preferably 1-10 $h^{-1}$, more preferably 2-6 $h^{-1}$.

In accordance with a preferred embodiment of the present disclosure, the crude caprolactam is obtained through the following mode: performing the gas phase Beckmann rearrangement reaction in the presence of a molecular sieve catalyst with a MFI structure, under a temperature of 320-420° C., a pressure of 0.05-0.5 MPa, a weight hourly space velocity of cyclohexanone oxime within a range of 1-10 $h^{-1}$, ethanol as a reaction solvent, and in the presence of a carrier gas, under any one of the technological process modes selected from the group consisting of a fixed bed reactor (having a weight hourly space velocity of cyclohexanone oxime less than 1 $h^{-1}$), a moving bed reactor (having a weight hourly space velocity of cyclohexanone oxime less than 1 $h^{-1}$), a fluidized bed reactor (having a weight hourly space velocity of cyclohexanone oxime about 5 $h^{-1}$), a fluidized bed reactor+a fixed bed reactor (having a weight hourly space velocity of cyclohexanone oxime about 5 $h^{-1}$), a fluidized bed reactor+a moving bed reactor (having a weight hourly space velocity of cyclohexanone oxime about 5 $h^{-1}$), subsequently performing the solvent recovery, removing a small amount of water from the reaction product, and removing light component impurities having a lower boiling point than caprolactam, to obtain crude caprolactam, wherein the content of caprolactam is not less than 98 wt %.

In the present disclosure, the carrier gas may be any gas that does not react with cyclohexanone oxime and the solvent under the conditions of gas phase Beckmann rearrangement reaction, for example, the carrier gas can be any inert gas known in the art, preferably nitrogen gas.

According to the present disclosure, the reaction solvent may be any existing solvent in the art, such as alcohol; preferably, the solvent for the gas phase Beckmann rearrangement reaction of cyclohexanone oxime is ethanol. The inventors of the present disclosure have discovered during the research process that complete discoloration of the impurities is difficult by using the conventional crystallization process under the normal conditions, because the impurities of the gas phase Beckmann rearrangement reaction product have a large number of varieties, deep color and poor chroma, the caprolactam needs to be distilled from the tower top by the subsequent distillation process, and the colored materials are retained in the tower bottom. Even then, sometimes the chroma of caprolactam is not ideal, thus the caprolactam product quality will be seriously affected ultimately. While the present disclosure can advantageously improve the yield and quality of caprolactam by using ethanol as the solvent for the gas phase Beckmann rearrangement reaction of cyclohexanone oxime, such that the selectivity of caprolactam is higher, the varieties and content of byproducts are reduced, in addition, the above problems can be well solved and the caprolactam product quality and yield can be further improved by combining the above specific refining processes of the present disclosure with a corresponding crystallization solvent containing a specific small amount of ethanol.

The present disclosure does not impose particular limitation on the crude caprolactam, and any crude caprolactam product obtained by the gas phase Beckmann rearrangement reaction of cyclohexanone oxime can be used in the present disclosure. In a preferred embodiment of the present disclosure, ethanol is used as the solvent for the gas phase Beckmann rearrangement reaction of cyclohexanone oxime, the crude caprolactam of step (1) further comprises at least one selected from the group consisting of cyclohexene, cyclohexadiene, acetonitrile, ethyl-acrylonitrile, propionitrile, ethoxy-cyclohexene, butyronitrile, ethyl-valeronitrile, cyclopentanone, ethyl cyclopentanone, valeronitrile, ethyl pyridine, ethyl hexenoate, ethoxy-1,3-cyclohexadiene, ethoxy-1,4-cyclohexadiene, cyclohexanone, hexanenitrile, cyanocyclopentane, ethyl-ε-hexylimide, ethyl-cyclohexanone, 5-cyano-1-pentene, ethoxy-cyclohexanone, cyclohexenone, cyclohexanol, phenol, bicyclo[3.1.0]-pentanone-2, N,N-diethyl-aniline, N-ethyl-aniline, phenylamine, ethyl-aniline, N-hexanamide, N-valeramide, valerolactam, N-ethyl-caprolactam, 1,2,3,4,5,6,7,8-octahydroacridine, 1,2,3,4,5,6,7,8 -octahydrophenazine, decahydrophenazine, 1,3,4,5-tetrahydro-2H-azepin-2-one and isomers thereof, 5,6,7,8-tetrahydro-2-naphthylamine and 1,2,3,4-tetrahydrocarbazole. The inventors of the present disclosure have discovered that the yield and quality of caprolactam can be further improved by using this preferred embodiment, while the prior art (for example, the relevant patent application submitted by the Sumitomo Corporation in Japan) generally uses methanol as the reaction solvent and the crude caprolactam obtained by removing heavy components as the crystallization feedstock, the crude caprolactam contains a large varieties of impurities, which are significantly different from the aforementioned varieties of impurities in the crude caprolactam of the present disclosure and cannot be easily separated and purified.

The crude caprolactam in the present disclosure may further comprise other unidentified impurities, the sum of the percentages of caprolactam and the impurities shall be 100%. The present disclosure does not impose limitation on the amount of impurities in the crude caprolactam, and each can be used in the present disclosure.

In the present disclosure, there is no limitation on the method for producing crude caprolactam having the above specified ingredients. It is preferable to use a solution that a solvent of gas phase Beckmann rearrangement of cyclohexanone oxime is ethanol to prepare the crude caprolactam having the above specified ingredients. The preferred solution provides a higher selectivity of caprolactam and is more conducive to improving yield and quality of caprolactam.

The present disclosure has a wide range for selecting the content of the individual components in the crude caprolactam, and it is preferable that the content of caprolactam is 98-99 wt %, the content of 1,2,3,4,5,6,7,8-octahydrophenazine is 0.01-0.3 wt %, the content of decahydrophenazine is 0.1-0.3 wt %, the content of 1,3,4,5-tetrahydro-2H-azepin-2-one and isomers thereof is 0.01-0.1 wt %, based on the total amount of the crude caprolactam. Due to a use of the preferred embodiment, the 1,2,3,4,5,6,7,8-octahydrophenazine, decahydrophenazine, 1,3,4,5-tetrahydro-2H-azepin-2-one and isomers thereof can be further converted into caprolactam through the subsequent hydrogenation process, thereby further increasing the yield of caprolactam.

According to a preferred embodiment of the present disclosure, as shown in FIG. 1, the process for refining caprolactam comprises the following steps:

(1) subjecting a crude caprolactam having a caprolactam content not less than 98 wt % to a first evaporative crystallization in the presence of a first crystallization solvent, so as to obtain a first slurry;

the crude caprolactam is obtained from the gas phase Beckmann rearrangement reaction product of cyclohexanone oxime through the solvent recovery, dehydration and removal of light components; the solvent for the gas phase Beckmann rearrangement reaction of cyclohexanone oxime is ethanol;

the first crystallization solvent comprises solvent A and optionally ethanol;

(2) subjecting the first slurry to a first solid-liquid separation to obtain a first caprolactam crystal and a first crystallization mother liquor;

(3) subjecting the first caprolactam crystal to a first washing to obtain a second caprolactam crystal and a first washing liquid;

the temperature of the first washing is not lower than the final temperature of the first evaporative crystallization;

the weight ratio of the used amount of washing solvent in the first washing relative to the first caprolactam crystal is 0.5-1.5:1;

(4) optionally concentrating the first crystallization mother liquor and then subjecting the concentrated first crystallization mother liquor to a second evaporative crystallization to obtain a second slurry;

the second evaporative crystallization has a final temperature that is 5-20° C. lower than the final temperature of the first evaporative crystallization; the second evaporative crystallization has a vacuum degree that is 5-20 kPa lower than the vacuum degree of the first evaporative crystallization;

(5) subjecting the second slurry to a second solid-liquid separation to obtain a third caprolactam crystal and a second crystallization mother liquor;

(6) subjecting the third caprolactam crystal to a second washing to obtain a fourth caprolactam and a second washing liquid;

the temperature of the second washing is not lower than the final temperature of the second evaporative crystallization;

the weight ratio of the used amount of washing solvent in the second washing relative to the third caprolactam crystal is 0.5-1.5:1;

(7) optionally concentrating the second crystallization mother liquor, then subjecting the concentrated second crystallization mother liquor to a thermostatic crystallization to obtain a third slurry, which is subjected to a third solid-liquid separation to obtain a fifth caprolactam crystal and a third crystallization mother liquor;

the thermostatic crystallization is carried out in the presence of a thermostatic crystallization solvent comprising solvent A and ethanol, the solubility of caprolactam in solvent A at a temperature of 20° C. is less than 5 wt %, and ethanol is less than 2 wt % of the total amount of thermostatic crystallization solvent; preferably, the solvent A is at least one selected from the group consisting of halogenated hydrocarbons, ethers and alkanes having 6-12 carbon atoms;

the temperature of said thermostatic crystallization is lower than the final temperature of the second evaporative crystallization, it is preferable that the temperature of the thermostatic crystallization is 5-20° C. lower than the final temperature of the second evaporative crystallization;

(8) subjecting the fifth caprolactam crystal to a third washing to obtain a sixth caprolactam crystal and a third washing liquid;

the weight ratio of the used amount of washing solvent in the third washing relative to the fifth caprolactam crystal is 0.5-1.5:1;

(9) subjecting the second caprolactam crystal obtained in step (3) to a hydrogenation reaction;

the hydrogenation reaction is performed in the presence of water and a hydrogenation catalyst; it is preferable that the used amount of water is 10-200 parts by weight, more preferably 10-40 parts by weight, relative to 100 parts by weight of the second caprolactam crystal; the hydrogenation catalyst is at least one selected from the group consisting of a nickel-based catalyst, a palladium-based catalyst and a platinum-based catalyst, preferably a nickel-based catalyst;

the conditions of hydrogenation reaction comprises a temperature of 50-150° C., a pressure of 0.2-2 MPa, and the hydrogen is used in an amount of 0.01-0.25 mole relative to 1 mole of the second caprolactam crystal;

(10) recycling the fourth caprolactam crystal and the sixth caprolactam crystal to step (1) and blend with the crude caprolactam to perform the first evaporative crystallization.

By using the refining process of the present disclosure, three crystallization processes can ensure that the yield of caprolactam is above 99%; and the produced caprolactam has a higher quality such that the industrially superior caprolactam can be obtained, in particular, caprolactam has potassium permanganate(PM) absorption value more than 10,000 s, caprolactam has an extinction value (at a wavelength of 290 nm) not more than 0.040, a volatile base value not more than 0.40 mmol/kg, a chroma value not more than 2, an acidity not more than 0.05 mmol/kg, an alkalinity not larger than 0.05 mmol/kg, the prepared caprolactam may be completely meet the requirements of the industrially superior product; while the caprolactam produced with the method of the prior art does not have both the high yield and the high quality, especially the caprolactam quality is far below the requirements of the industrially superior product.

As previously mentioned, a second aspect of the present disclosure provides a refining system of caprolactam comprising a first evaporative crystallizer, a first solid-liquid separation device and a first washing device connected in series, wherein an outlet of the first evaporative crystallizer is in communication with an inlet of the first solid-liquid separation device, and the solid phase outlet of the first solid-liquid separation device is in communication with an inlet of the first washing device;

the system further comprises a second evaporative crystallizer, a second solid-liquid separation device and a second washing device successively connected in series, wherein an inlet of the second evaporative crystallizer is in communication with the liquid phase outlet of the first solid-liquid separation device, an outlet of the second evaporative crystallizer is in communication with an inlet of the second solid-liquid separation device, and a solid phase outlet of the second solid-liquid separation device is in communication with an inlet of the second washing device; optionally a first solvent recovery column is disposed at the communication pipeline between an inlet of the second evaporative crystallizer and the liquid phase outlet of the first solid-liquid separation device;

the system further comprises a thermostatic crystallizer, a third solid-liquid separation device and a third washing device connected in series, wherein an inlet of the thermostatic crystallizer is in communication with the liquid phase outlet of the second solid-liquid separation device, an outlet of the thermostatic crystallizer is in communication with an inlet of the third solid-liquid separation device, the solid phase outlet of the third solid-liquid separation device is in communication with an inlet of the third washing device; optionally a second solvent recovery column is arranged at the communication pipeline between an inlet of the thermostatic crystallizer and the liquid phase outlet of the second solid-liquid separation device;

the system further comprises a hydrogenation reactor, an inlet of the hydrogenation reactor is in communication with the solid phase outlet of the first washing device.

The present disclosure does not impose limitation on the specific equipment type of the first evaporative crystallizer, the first solid-liquid separation device, the corresponding washing device (including the first washing device, the second washing device, the third washing device), the second evaporative crystallizer, the second solid-liquid separation device, the thermostatic crystallizer, the third solid-liquid separation device and the hydrogenation reactor, as long as the aforementioned specific first evaporative crystallization, first solid-liquid separation, washing, second evaporative crystallization, second solid-liquid separation, corresponding washing, thermostatic crystallization, third solid-liquid separation and hydrogenation reaction can be realized, the skilled person in the art can freely choose it according to the practical requirements; for example, the first evaporative crystallizer and the second evaporative crystallizer each may be independently an adiabatic evaporator, and the first solid-liquid separation device and the corresponding washing device can be respectively and separately operated by two equipment (for example, both a washing tank and a centrifuge), or can be simultaneously performed on an equipment (for example, a filter press or a counter-current washing device) by means of a counter-current washing mode. The present disclosure has no limitation on the specific equipment of the optionally first solvent recovery column and the optionally second solvent recovery column, as long as the concentration can be performed.

In the present disclosure, the technological process conditions of the first evaporative crystallizer, the first solid-liquid separation device, the respective washing devices (including the first washing device, the second washing device, the third washing device), the second evaporative crystallizer, the second solid-liquid separation device, the thermostatic crystallizer, the third solid-liquid separation device, and the hydrogenation reactor, and optionally the first solvent recovery column and optionally the second solvent recovery column are identical with the corresponding steps in the first aspect mentioned above, thus the content is not repeated here.

According to the present disclosure, it is preferable that the liquid phase outlet of the first washing device is in communication with an inlet of the first evaporative crystallizer and/or the second washing device, in order to circulate the liquid phase material obtained after the first washing and use it in the first evaporative crystallization and/or in the second washing as a washing solvent of the second washing.

According to the present disclosure, it is preferable that the liquid phase outlet of the second washing device is in communication with an inlet of the third washing device, so as to use the liquid phase material obtained after the second washing as a washing solvent of the third washing for the third washing.

According to the present disclosure, it is preferable that the liquid phase outlet of said third washing device is in communication with the thermostatic crystallizer. In the present disclosure, the liquid outlet of the third washing device may be in direct or indirect communication with the thermostatic crystallizer; for example, as shown in FIG. 1, the liquid outlet of the third washing device is preferably first in communication with the second solvent recovery column, which is in communication with the thermostatic crystallizer to concentrate the liquid material obtained after the third washing and subsequently perform the thermostatic crystallization in a cyclic manner to further increase the caprolactam yield.

According to the present disclosure, it is preferable that the solid phase outlet of the second washing device and the solid phase outlet of the third washing devices are respectively in communication with an inlet of the first evaporative crystallizer, so as to recycle the fourth caprolactam and the sixth caprolactam crystal to step (1) and blend with the crude caprolactam to carry out the first evaporative crystallization.

The refining system of caprolactam provided by the present disclosure is capable of carrying out the specific refining process of the first aspect, and can obtain the caprolactam with high yield and quality.

The present disclosure will be described in detail with reference to examples. In the examples and preparation examples below, the raw materials involved therein are commercially available, unless otherwise specified.

In the present disclosure, the content of the metallic element was measured by using an inductively coupled plasma (ICP) atomic emission spectrometer 7000DV, manufactured by PE (Perkin Elmer Incorporation) of the USA, under the test conditions as follows: the molecular sieve was dissolved by using HF acid to completely dissolve silicon oxide and metal oxide in the sample, and the content of metal ions was measured in an aqueous solution.

The external specific surface area and the BET specific surface area of the molecular sieve were measured by an automatic adsorption apparatus with a model number ASAP-2460 manufactured by the Micromeritics Instrument Corporation in the USA, under the following test conditions: $N_2$ was used as an adsorbate, the adsorption temperature was −196.15° C. (liquid nitrogen temperature), and degassing was performed at 1.3 Pa and the constant temperature 300° C. for 6 hours.

The X-ray diffraction spectrum was recorded by a Miniflex600 type diffractometer manufactured by the Rigaku Corporation in Japan, and the test conditions were as follows: Cu target Kα radiation, Ni optical filter, the tube voltage was 40 kV, the tube current was 40 mA;

The prepared sample was analyzed by a field emission scanning electron microscope with a model number S-4800 manufactured by the Hitachi Corporation of Japan.

The particle size and particle size distribution of the catalyst were measured by a 2000E type laser particle size analyzer manufactured by the Dandong Bettersize Instruments Co., Ltd., the test method was a wet process test, water was used as a medium, and the mass concentration of a sample was within a range of 0.5% -2%, the scanning speed was 2,000 times/second;

The mist spray forming was carried out in a mist spray forming apparatus with a model number LT-300 manufactured by the Wuxi Tianyang Spray Drying Equipment Co., Ltd.;

In the following examples, the test methods below were used to evaluate the relevant parameters of the prepared caprolactam crystal and caprolactam product (1) Purity of ε-caprolactam The purity of ε-caprolactam was measured by the gas chromatographic method, the gas chromatography was 7890GC, the capillary column was Innowax 60 m, and the minimum chromatography detection limit was 0.1 μg/g.

(2) Potassium permanganate value (PM value) of caprolactam

The potassium permanganate value of caprolactam can be measured by visual comparison with a standard solution, which is composed of 3 g $Co(NO_3)_2 \cdot 6H_2O$ and 0.012 g $K_2Cr_2O_7$ in 1 L of water. One milliliter of 0.01 mol/L potassium permanganate solution is added to 100 mL of 3 wt % aqueous caprolactam solution at 20° C. The time (s) taken for the color to change to that of the standard solution is referred to as the potassium permanganate value.

(3) Volatile Basicity (VB)

In the alkaline medium, the alkaline low molecular impurities in the sample were distilled out and absorbed with a known amount of hydrochloric acid solution, and the excess hydrochloric acid was dripped back with the sodium hydroxide standard solution. The mole number of consumed acid amount per kilogram of sample was used as the measured value of the volatile base. The computational formula was as follows:

$$VB\ (mmol/kg) = [(V_0 - V) \times C_{NaOH}/M] \times 1000$$

Where: $V_0$ was the volume of NaOH standard solution consumed in the blank test, the unit was mL;

V was the volume of NaOH standard solution consumed by the sample, the unit was mL;

$C_{NaOH}$ was the accurate concentration of NaOH standard solution, the unit was mol/L;

M was the sample mass, and the unit was gram (g).

(4) Extinction value E (at a wavelength of 290 nm)

50 g of caprolactam was weighed and placed in a 300 ml Erlenmeyer flask, 50 ml of distilled water was added, shaken to completely dissolve the sample, and allowed to stand for 10 minutes. Using a spectrophotometer, at a wavelength of 290 nm, the extinction value of the sample with a concentration of 50% relative to distilled water was detected.

(5) Chroma Value

Caprolactam (50 g) was weighed and placed in a 300 ml Erlenmeyer flask, 50 ml of distilled water was added, shaken to completely dissolve the sample, and allowed to stand for 10 minutes. Then a light absorbance value through the solution of UV ray having a wavelength of 390 nm was measured using water as a refence solution, respectively.

(6) Potential of Hydrogen (pH)

The caprolactam sample was dissolved in water, the methyl red-methylene blue was used as an indicator, the free acid or free base in the sample was titrated with hydrochloric acid or sodium hydroxide. The computational formula was as follows:

$$\text{Acidity (mmol/kg)} = (V \times C_{HCl})/M \times 1000$$

$$\text{Alkalinity (mmol/kg)} = (V \times C_{NaOH})/M \times 1000$$

Where: V was the volume of standard solution consumed by the sample in mL;

$C_{HCl}$ was the accurate concentration of the HCl standard solution in mol/L;

$C_{NaOH}$ was the accurate concentration of NaOH standard solution in mol/L;

M was the sample mass in the unit of gram (g).

Preparation Example 1

The preparation example aimed to illustrate a process of preparing the crude caprolactam of the present disclosure.

1. Preparation of the molecular sieve catalyst with a MFI Structure (mist spray forming)

(1) 482 kg of ethanol with a content of 95 wt % and 302 kg of tetrapropylammonium hydroxide aqueous solution with a content of 22.5 wt % were respectively added into a stainless steel reaction kettle having a volume of 2 m³, the ingredients were stirred, 347 kg of ethyl orthosilicate was then supplemented, the stirring process was continued, 332 kg of water and 38.6 g of $Fe(NO_3)_3 \cdot 9H_2O$ were further added, and the stirring process was continued for 4 hours under the normal temperature, so that a colloid mixture was obtained; wherein the molar ratio of ethyl orthosilicate calculated by $SiO_2$: ethanol: tetrapropylammonium hydroxide: water was 1:10:0.2:20; the weight ratio of ethyl orthosilicate calculated by $SiO_2$ relative to the metal source calculated by metallic element was 18,666:1;

(2) the colloid mixture was subjected to crystallization with an ethanol-hydrothermal system, wherein the crystallization conditions comprise: crystallization was initially performed at 70° C. for 1 day, and crystallization was then performed at 100° C. for 2 days, such that the crystallization mother liquor with a pH of 13.51 was obtained;

(3) the obtained crystallization mother liquor was subjected to evaporating at 85° C. for 10 hours to evaporate ethanol (water was supplemented continuously during the evaporation process, so as to maintain the material at a certain liquid level, and recover water-containing ethanol solution for use); then a 50 nm six-tube membrane was used for washing and concentrating the crystallization mother liquor, the washing was performed by means of water with a temperature of 40-60° C., wherein the used amount of the washing water was 6.0M³, and the washing process was continued until a pH of the washing water of the crystallized product reached 9.1. Following the washing and concentrating process, 395 kg of molecular sieve slurry with a solid content of 26.8 wt % was obtained.

A small amount of the molecular sieve slurry was taken and subjected to drying at 120° C. for 20 hours, the dried molecular sieve slurry was then subjected to roasting at 550° C. for 6 hours to produce the molecular sieve, wherein the molecular sieve had a metal element content of 51.5 μg/g, a BET specific surface area of 426 m²/g, and an external specific surface area of 44 m²/g;

as shown in the X-ray diffraction spectrogram of the molecular sieve, the X-ray diffraction (XRD) spectrogram was consistent with the characteristics of MFI structure standard XRD spectrogram recorded in *Microporous Materials, Vol.* 22, p637, 1998, it demonstrated that the molecular sieve had a MFI crystal structure;

as can be seen from the transmission electron microscope (TEM) photograph that the MFI topological structure molecular sieve had uniform crystalline grain particle size and a particle size of 0.15-0.2 μm;

(4) the part of the molecular sieve slurry obtained in step (3) was mixed with 201 kg of alkaline silica sol with the content of 30 wt % (the pH was 9.5, the content of sodium ions was 324 ppm, the content of $SiO_2$ was 40 wt %, and the surface area of $SiO_2$ obtained after roasting was 225 m²/g), wherein the weight ratio of the molecular sieve based on the dry weight relative to the alkaline silica sol calculated by $SiO_2$ was 60:40, the mixture was stirred uniformly and pulped to obtain molecular sieve-binder slurry with the solid content of 25.2 wt %. The molecular sieve-binder slurry was conveyed to a mist spray forming device for performing the mist spray forming, wherein the inlet temperature and the outlet temperature of the mist spray forming device were 260° C. and 135° C. respectively. The mixture was then fed into a 3M³ heating shuttle furnace (manufactured by Hubei Huanggang Huaxia Electromechanical Thermal Equipment Co., Ltd., hereinafter the same), and subjected to roasting at 280° C., 400° C. and 480° C. for 2 h respectively, and finally subjected to roasting at 550° C. for 12 h to obtain 149.5 kg microsphere molecular sieve, wherein the content of the MFI topological structure silicon molecular sieve containing a trace amount of metal ions with Lewis acid characteristic was 60 wt %, and the content of the binder calculated by $SiO_2$ was 40 wt %;

100 g of the microspherical molecular sieve and 1,000 g of the alkaline buffer solution of a nitrogen-containing compound (the alkaline buffer solution of a nitrogen-containing compound was a mixed solution of ammonia water and an ammonium nitrate aqueous solution, wherein the pH was 11.35, the content of the ammonia water was 26 wt %, the content of the ammonium nitrate in the ammonium nitrate aqueous solution was 7.5 wt %, the weight ratio of the ammonia water relative to the ammonium nitrate aqueous solution was 3:2) were added into a stainless steel reaction kettle having a volume of 2,000 ml (KCF-2 type magnetic stirring autoclave, manufactured by the Keli Automatic Control Equipment Research Institute of Yantai High-tech Zone, hereinafter the same), the mixture was subjected to stirring at a constant temperature of 86° C. and under a pressure of 2.7 kg/cm² for 2 hours, then subjected to filtering, and drying at 90° C. for 12 hours, the operations were then repeated once under the same conditions, and subjected to filtering, and washing until the pH of a filtration clear solution was about 9, and subsequently subjected to drying at 120° C. for 24 hours to prepare the catalyst S1 (i.e., the molecular sieve catalyst having a MFI structure). The photograph of catalyst S1 was shot, and it can be seen from the photograph that the particle size of the catalyst was very uniform; the catalyst S1 was subjected to the TEM measurement, the TEM photograph showed that the tiny particles of 10-30 nm existed on the crystalline grains of the MFI topological structure all-silicon molecular sieve, and the tiny particles were silicon oxide binder.

The particle size distribution of the catalyst was shown in Table 1, the particle size of the catalyst was concentrated within a range of 70-150 μm, and the abrasion index K was 1.6%/h.

TABLE 1

| Particle size μM | Range % | Accumulation % | Particle size μM | Range % | Accumulation % |
|---|---|---|---|---|---|
| 0.040-0.044 | 0.00 | 0 | 8.944-9.966 | 0.61 | 6.88 |
| 0.044-0.049 | 0.00 | 0 | 9.966-11.10 | 0.62 | 7.5 |
| 0.049-0.055 | 0.00 | 0 | 11.10-12.37 | 0.62 | 8.12 |
| 0.055-0.061 | 0.00 | 0 | 12.37-13.78 | 0.63 | 8.75 |
| 0.061-0.068 | 0.00 | 0 | 13.78-15.36 | 0.67 | 9.42 |
| 0.068-0.076 | 0.00 | 0 | 15.36-17.11 | 0.74 | 10.16 |
| 0.076-0.085 | 0.00 | 0 | 17.11-19.07 | 0.84 | 11 |
| 0.085-0.095 | 0.00 | 0 | 19.07-21.25 | 0.98 | 11.98 |
| 0.095-0.105 | 0.00 | 0 | 21.25-23.68 | 1.15 | 13.13 |
| 0.105-0.118 | 0.00 | 0 | 23.68-26.39 | 1.36 | 14.49 |
| 0.118-0.131 | 0.00 | 0 | 26.39-29.40 | 1.64 | 16.13 |
| 0.131-0.146 | 0.00 | 0 | 29.40-32.76 | 2.03 | 18.16 |
| 0.146-0.163 | 0.00 | 0 | 32.76-36.50 | 2.57 | 20.73 |
| 0.163-0.181 | 0.00 | 0 | 36.50-40.68 | 3.28 | 24.01 |
| 0.181-0.202 | 0.00 | 0 | 40.68-45.33 | 4.17 | 28.18 |
| 0.202-0.225 | 0.00 | 0 | 45.33-50.51 | 5.16 | 33.34 |
| 0.225-0.251 | 0.00 | 0 | 50.51-56.28 | 6.21 | 39.55 |
| 0.251-0.280 | 0.00 | 0 | 56.28-62.71 | 7.16 | 46.71 |
| 0.280-0.312 | 0.00 | 0 | 62.71-69.87 | 7.88 | 54.59 |
| 0.312-0.348 | 0.00 | 0 | 69.87-77.86 | 8.19 | 62.78 |
| 0.348-0.388 | 0.00 | 0 | 77.86-86.76 | 7.99 | 70.77 |
| 0.388-0.432 | 0.00 | 0 | 86.76-96.67 | 7.40 | 78.17 |
| 0.432-0.481 | 0.00 | 0 | 96.67-107.7 | 6.44 | 84.61 |
| 0.481-0.536 | 0.00 | 0 | 107.7-120.0 | 5.26 | 89.87 |
| 0.536-0.598 | 0.00 | 0 | 120.0-133.7 | 3.97 | 93.84 |
| 0.598-0.666 | 0.00 | 0 | 133.7-149.0 | 2.78 | 96.62 |
| 0.666-0.742 | 0.00 | 0 | 149.0-166.0 | 1.75 | 98.37 |
| 0.742-0.827 | 0.00 | 0 | 166.0-185.0 | 1.00 | 99.37 |
| 0.827-0.922 | 0.00 | 0 | 185.0-206.1 | 0.49 | 99.86 |
| 0.922-1.027 | 0.00 | 0 | 206.1-229.7 | 0.13 | 99.99 |
| 1.027-1.144 | 0.00 | 0 | 229.7-255.9 | 0.01 | 100 |
| 1.144-1.275 | 0.00 | 0 | 255.9-285.2 | 0.00 | 100 |
| 1.275-1.421 | 0.00 | 0 | 285.2-317.8 | 0.00 | 100 |
| 1.421-1.583 | 0.04 | 0.04 | 317.8-354.1 | 0.00 | 100 |
| 1.583-1.764 | 0.11 | 0.15 | 354.1-394.6 | 0.00 | 100 |
| 1.764-1.966 | 0.16 | 0.31 | 394.6-439.7 | 0.00 | 100 |
| 1.966-2.191 | 0.17 | 0.48 | 439.7-489.9 | 0.00 | 100 |
| 2.191-2.441 | 0.19 | 0.67 | 489.9-545.9 | 0.00 | 100 |
| 2.441-2.720 | 0.25 | 0.92 | 545.9-608.3 | 0.00 | 100 |
| 2.720-3.031 | 0.29 | 1.21 | 608.3-677.8 | 0.00 | 100 |
| 3.031-3.377 | 0.33 | 1.54 | 677.8-755.3 | 0.00 | 100 |
| 3.377-3.763 | 0.39 | 1.93 | 755.3-841.6 | 0.00 | 100 |
| 3.763-4.193 | 0.41 | 2.34 | 841.6-937.7 | 0.00 | 100 |
| 4.193-4.673 | 0.47 | 2.81 | 937.7-1044 | 0.00 | 100 |
| 4.673-5.207 | 0.52 | 3.33 | 1044-1164 | 0.00 | 100 |
| 5.207-5.802 | 0.57 | 3.9 | 1164-1297 | 0.00 | 100 |
| 5.802-6.465 | 0.58 | 4.48 | 1297-1445 | 0.00 | 100 |
| 6.465-7.203 | 0.60 | 5.08 | 1445-1610 | 0.00 | 100 |
| 7.203-8.026 | 0.60 | 5.68 | 1610-1794 | 0.00 | 100 |
| 8.026-8.944 | 0.59 | 6.27 | 1794-2000 | 0.00 | 100 |

2. Preparation of the molecular sieve catalyst with a MFI Structure (rotary molding)

(1) 482 kg of ethanol with a content of 95 wt % and 302 kg of tetrapropylammonium hydroxide aqueous solution with a content of 22.5 wt % were respectively added into a stainless steel reaction kettle having a volume of 2M³, the ingredients were stirred, 347 kg of ethyl orthosilicate was then supplemented, the stirring process was continued for 30 min, 332 kg of water and 38.65 g of $Fe(NO_3)_3 \cdot 9H_2O$ were further added, and the stirring process was continued for 4 hours under the normal temperature, so that a colloid mixture was formed; wherein the molar ratio of ethyl orthosilicate calculated by $SiO_2$: ethanol:tetrapropylammonium hydroxide:water was 1:10:0.2:20; the weight ratio of ethyl orthosilicate calculated by $SiO_2$ relative to the metal source calculated by metallic element was 18,666:1;

(2) the colloid mixture was subjected to crystallization with an ethanol-hydrothermal system, wherein the crystallization conditions comprise: crystallization was initially performed at 70° C. for 1 day, and crystallization was then performed at 100° C. for 2 days, such that the crystallization mother liquor was obtained;

(3) the crystallization mother liquor was subjected to washing and filtering, then drying at 120° C. for 24 hours, about 135.5 kg of molecular sieve raw powder was obtained;

a suitable amount of the molecular sieve raw powder was taken and subjected to roasting at 550° C. for 6 hours to obtain the molecular sieve sample, wherein the content of metal element was 49.4 ppm, the BET specific surface area was 426 $m^2/g$, and the external specific surface area was 44 $m^2/g$; the X-ray diffraction spectrogram of the product illustrated that the X-ray diffraction (XRD) spectrogram was consistent with the characteristics of MFI structure standard XRD spectrogram recorded in *Microporous Materials, Vol.* 22, p637, 1998, it demonstrated that the molecular sieve had a MFI crystal structure;

as can be seen from the transmission electron microscope (TEM) photograph that the MFI topological structure molecular sieve had uniform crystalline grain particle size and a particle size of 0.1-0.2 μm;

(4) the molecular sieve raw powder was pulverized, 2 kg of the pulverized molecular sieve raw powder was taken and sieved to 100-1,000 mesh powder sample, which was placed in a rotary table forming machine, wherein the rotary table forming machine (a sugar-coating machine with a model number BY-1200, manufactured by the Tiantai Pharmaceutical Machinery Factory Corporation in Taizhou City, Jiangsu Province of China) had a rotary table diameter of 1.2 m, a rotary table depth of 450 mm, an inclination angle of the rotary table determined to be 50°, and a rotary speed of the rotary table was set to be 30 rpm. 1.5 kg deionized water was sprayed into the rotary table to obtain the first spherical particles having a particle diameter about 0.2-0.8 mm;

furthermore, 110 kg of the powder sample sieved to 200-800 mesh was mixed uniformly with 50 kg of alkali silica sol (having a sodium ion content of 543 ppm, and a $SiO_2$ content of 30 wt %) in a weight ratio of 2.2:1, the mixture was pulverizing again, the particles less than 30 mesh were taken, 160 kg of particles less than 30 mesh were added at a constant speed into the rotary table forming machine having the first spherical particles, the adding process was completed within 240 min; and then subjected to sieving by means of the sieves of 12 mesh and 9 mesh, about 100 kg spherical particles having a particle diameter of 1.5-2 mm was obtained;

(5) the obtained 100 kg spherical particles were blown with wind at 45° C., extremely small quantity of water were supplemented for several times during the process, after being tightened for 2 hours, the particles were subjected to drying at 120° C. for 24 hours, and then subjected to roasting at 550° C. for 10 hours to obtain 72 kg of roasted product with a molecular sieve content of 86%;

45 kg of the roasted product with 450 kg of alkaline buffer solution (the alkaline buffer solution was a mixed solution of ammonia water and an ammonium nitrate aqueous solution, wherein the content of the ammonia water was 26 wt %, the content of the ammonium nitrate in the ammonium nitrate aqueous solution was 7.5 wt %, the weight ratio of the ammonia water relative to the ammonium nitrate aqueous solution was 3:2, the pH of said alkaline buffer solution was 11.35) were added into a pressurized reaction kettle having a volume of $1M^3$, the ingredients were stirred at a temperature of 82° C. and a pressure 2.3 $kg/cm^2$ for 1.5 hours, and then subjected to washing, filtering and drying to obtain a spherical catalyst S2;

the catalyst had a particle diameter within a range of 1.4-1.8 mm and a crush strength of 28N/particle.

3. Preparation of Crude Caprolactam

The crude caprolactam was prepared through the gas phase Beckmann rearrangement from the raw materials cyclohexanone oxime, ethanol and nitrogen in the presence of water and catalyst, the gas phase Beckmann rearrangement of cyclohexanone oxime was performed in a home-made fixed fluidized bed reaction unit (a vertical type reactor having a volume of 316 L made of the material stainless steel, wherein the upper segment had a diameter 20 cm, the lower segment had a diameter of 10 cm, the upper segment and the lower segment had a length of 60 cm and 80 cm, respectively), wherein the fixed fluidized bed reaction unit was filled with 300 g of the prepared and obtained catalyst S1 mentioned above; the vertical type fixed fluidized bed reaction unit having a volume of 316 L made of the material stainless steel was in communication with a catalyst regeneration reactor for regenerating the catalyst discharged from the fixed fluidized bed reaction unit and then recycling the regenerated catalyst, the catalyst regeneration reactor was provided with a structure consisting of a diameter of 15 cm, a length of 160 cm, and a charged amount of 550 g catalyst; the conditions of the fixed fluidized bed reaction unit were as follows: the reaction pressure was 0.1 MPa, the reaction temperature was 380° C., the feedstock was fed by means of the gas atomization and mist spray, a vaporizer temperature was controlled at 190° C., the temperature of a pipeline was kept at 250° C., the weight hourly space velocity (WHSV) of cyclohexanone oxime was 5 $h^{-1}$, the nitrogen gas flow rate was $0.8M^3/h$, the concentration of cyclohexanone oxime in cyclohexanone oxime and ethanol was 35 wt %; the water content relative to the total amount of water, ethanol and cyclohexanone oxime was 0.4 wt %.

The reaction outlet of the fixed fluidized bed reaction unit was connected to a continuous flow fixed bed reactor. The conditions of the continuous flow fixed bed reactor were as follows: the inside diameter of the reactor was 28 mm, the prepared spherical catalyst S2 mentioned above was filled, the loading amount of catalyst was 80 g; the bed layer had a height of 30 cm; the reaction pressure was 0.1 MPa; the reaction temperature was 380° C-390° C.; the weight hourly space velocity (WHSV) of cyclohexanone oxime was 0.5 $h^{-1}$. The unconverted cyclohexanone oxime in an amount of less than 5 wt % in the product obtained from the fixed fluidized bed reactor was nearly 100% converted in the continuous flow fixed bed reactor.

The reaction was performed for 60 h, the obtained Beckmann rearrangement reaction product was initially subjected to water cooling, and then subjected to secondary cooling by circulation of a glycol solution at −10° C. to collect the reaction product and obtain a mixture of ethanol solution containing caprolactam.

1.6 kg of the above mixture was taken, the solvent (ethanol) recovery was carried out by using a rotary evaporator, 618.5 g crude caprolactam product containing impurities having a higher boiling point than caprolactam and impurities having a lower boiling point than caprolactam was obtained, the crude caprolactam product was analyzed the analysis result indicated that its main ingredients were as follows: 95.8 wt % of caprolactam and other impurities. Among them, the sample analysis was carried out by a gas chromatograph (hydrogen flame ion detector, PEG20M capillary chromatographic column, column length 50 m) with a model number 6890 manufactured by the Agilent Technologies Company.

The crude caprolactam product was subjected to dehydration and the treatment of removing light impurities; the crude caprolactam product was subjected to the vacuum distillation (16 tower trays and inverted triangular metal packing) at a pressure (absolute pressure) of 4.5 kPa and heated from room temperature (20° C.) to 100° C. at a temperature rise rate of 2° C./min and the temperature 100° C. was kept for 30 min, total reflux on the tower top, and the temperature was further increased to 120° C. at a temperature rise rate of 2° C./min, and the pressure was decreased directly to 3.0 kPa, the tower top reflux ratio was 1:20 until there was no light components were distilled to produce 560 g of product obtained after removing light component (kettle bottom material, i.e., crude caprolactam).

The crude caprolactam was subjected to the sample analysis, the analysis result indicated that the crude caprolactam was consisting of the main components as follows: 98.4 wt % of caprolactam, 240 μg/g of 5-cyano-1-pentene, 210 μg/g of cyclohexanone oxime, 1,100 μg/g of cyclohexenone, 1,100 μg/g of N-ethyl-caprolactam, 470 μg/g of 1,2,3,4,5,6,7,8-octahydrophenazine, 360 μg/g of 1,3,4,5-tetrahydro-2H-azepin-2-one and isomers thereof, 1,200 μg/g of decahydrophenazine, 70 μg/g of 5,6,7,8-tetrahydro-2-napthalenamine, 50 μg/g of 1,2,3,4-tetrahydrocarbazole and other unidentified impurities.

Preparation Example 2

The process of refining caprolactam was performed according to the process of the preparation example 1, and the corresponding tests were performed, except that the same amount of methanol was used as the reaction solvent, and the other components and steps were identical with those of the preparation example 1.

The crude caprolactam was subjected to the sample analysis, the analysis result indicated that the crude caprolactam was consisting of the main components as follows: 98.5 wt % of caprolactam, 270 μg/g of 5-cyano-1-pentene, 260 μg/g of cyclohexanone oxime, 1,500 μg/g of cyclohexenone, 1,800 μg/g of N-ethyl-caprolactam, 430 μg/g of 1,2,3,4,5,6,7,8-octahydrophenazine, 200 μg/g of 1,3,4,5-tetrahydro-2H-azepin-2-one and isomers thereof, 1,200 μg/g of decahydrophenazine, 80 μg/g of 5,6,7,8-tetrahydro-2-napthalenamine, 100 μg/g of 1,2,3,4-tetrahydrocarbazole and other unidentified impurities.

The refining process and the refining system of the present disclosure were illustrated with reference to examples. In the examples below, the component of the mixed solvent other than ethanol was a solvent A, the solvent A in each of the following examples satisfied a condition that the solubility of caprolactam in the solvent A was less than 5 wt % at 20° C.

EXAMPLE 1

The example adopted a refining process as follows:
(1) First evaporative crystallization: the crude caprolactam (400 parts by weight) prepared and obtained from the preparation example 1 and a mixed solvent (i.e., a first crystallization solvent, 900 parts by weight) consisting of 9 parts by weight of ethanol and 891 parts by weight of isopropyl ether were sufficiently blended in an adiabatic glass crystallization kettle (i.e., a first evaporative crystallizer), the crude caprolactam was thoroughly dissolved in the mixed solvent with a temperature of 62° C., when the temperature inside the crystallization kettle was slowly decreased to 60° C., the vacuumization process was started in the crystallization kettle, an evaporative crystallization was performed, the operating pressure was controlled to be 65 kPa, the amount of evaporation was controlled, the solvent was uniformly evaporated; the operating pressure was adjusted while the solvent was continuously volatilized, the temperature of the liquid phase in the crystallization kettle was decreased accordingly, the operating pressure was controlled to be 38 kPa when the temperature of the solution in the crystallization kettle was lowered to 45° C.; 2 wt % of pure caprolactam at 20-30 meshes was added into the solution as the seed crystal when the temperature of the crystallization kettle was decreased to 44° C., the caprolactam started to precipitate at 43° C., the solvent was continuously extracted, the operating pressure was adjusted according to the practical condition; when the temperature of the solution in the crystallization kettle was decreased to 35° C., the vacuumization was performed and the operating pressure was controlled to be 26 kPa (i.e., the final vacuum degree or final pressure), the solvent was further extracted; when the temperature of the solution inside the crystallization kettle was lowered to 30° C. (i.e., the final temperature), the vacuumization was stopped, the temperature was maintained at 30° C. for 45 min (i.e., the residence time), and the experiment was terminated.

(2) First solid-liquid separation, first washing: the caprolactam slurry obtained in step (1) (i.e., a first slurry, 1,300 parts by weight) was pumped from the crystallization kettle to a centrifuge (i.e., a first solid-liquid separation device and a first washing device) to perform a first solid-liquid separation, in order to obtain a first caprolactam crystal and a first crystallization mother liquor. The solid phase obtained in step (2) (i.e., a first caprolactam crystal) was washed with the mixed solvent (330 parts by weight; with the same temperature as the final temperature of first evaporative crystallization) consisting of the same components in the same proportions as defined above, the solid-liquid separation was then continued to obtain a caprolactam crystal (i.e., a second caprolactam crystal, 330 parts by weight) and a liquid phase (i.e., a first washing liquid, 1,300 parts by weight).

(3) Second evaporative crystallization: the first crystallization mother liquor (with a caprolactam content of 10 wt %) obtained from the first solid-liquid separation was poured into a crystallization tank (i.e., a second evaporative crystallizer) before the crystals was started to precipitate, the inter-layer water bath temperature in the crystallization tank was 40° C., the first crystallization mother liquor was subjected to stirring and stabilizing and then concentrated at 30-35 kPa till the caprolactam concentration was increased to 18 wt %, the seed crystals (identical with the seed crystals in the first evaporative crystallization) were added, the caprolactam crystal started to precipitate, the vacuumization was stopped, the operating pressure was controlled at 19 kPa (i.e., the final vacuum degree or the final pressure), the inter-layer water bath was maintained at 40° C. for 30 min, then reduced to 20° C. (i.e., the final temperature) at a cooling rate of 0.2-0.5° C./min, and the temperature was maintained at 20° C. for 30 min to obtain a second slurry.

(4) Second solid-liquid separation, second washing: the second slurry was delivered to a centrifuge (i.e., a second solid-liquid separation device and a second washing device) for performing a second solid-liquid separation, a third caprolactam crystal and a second crystallization mother liquor were obtained respectively; the third caprolactam crystal was subjected to a second washing process under the same conditions as the washing process of a solid phase obtained by solid-liquid separation after the first evaporative crystallization in this example, the temperature of the second washing was the same as a final temperature of the second evaporative crystallization, and the solid-liquid separation was then performed to obtain a fourth caprolactam and a second washing liquid.

(5) Thermostatic crystallization: the second crystallization mother liquor (with the caprolactam content of 9 wt %) obtained from the second solid-liquid separation was subjected to concentrating under the temperature of 30° C., 20-25 KPa till the caprolactam content in the second crystallization mother liquor was increased to 18 wt %, the seed crystal (the same seed crystal as that in the first evaporative crystallization) was added, the caprolactam crystal was precipitated, the vacuumization was stopped, the inter-layer water bath was maintained at 30° C. for 30 min, the temperature was then decreased to 10° C. at the temperature fall rate of 0.2-0.5° C./min, the temperature was kept at 10° C. for 30 min to perform the thermostatic crystallization and obtain a third slurry, the third slurry was then subjected to a third solid-liquid separation in a centrifuge (i.e., a third solid-liquid separation device and third washing device) to obtain a fifth caprolactam crystal and a third crystallization mother liquor, respectively, the fifth caprolactam crystal was subjected to a third washing under the same washing conditions as the solid phase obtained by the solid-liquid separation after the first evaporative crystallization, the temperature of the third washing was identical with the temperature of said thermostatic crystallization, the solid-liquid separation was subsequently performed to obtain a sixth caprolactam crystal and a third washing liquid. The third washing liquid was mixed with the second crystallization mother liquor to joint perform the thermostatic crystallization.

The purity of the fourth caprolactam obtained in step (4) was 99.9%, and the purity of the sixth caprolactam crystal obtained in step (5) was 99.5% or more.

The caprolactam yield of the first crystallization was 82.3%, the caprolactam yield of the first crystallization mother liquor was 13.3%, the caprolactam yield of the second crystallization mother liquor was 3.5%, thus the total caprolactam yield was 99.1%

(6) Hydrogenation reaction: 150 g of the caprolactam crystal (i.e., the second caprolactam crystal with a purity of 99.9930 wt %) was added to a 500 mL reaction kettle (i.e., a hydrogenation reactor) and 37.5 g of water was added, 1.5 g of an amorphous nickel hydrogenation catalyst (manufactured by the Sinopec Catalyst Changling Branch with the industrial trade name SRNA-4) was further added, the mixture was heated to about 75° C., hydrogen gas was then introduced, the hydrogen gas flow rate was controlled at 100 mL/min, the reaction pressure was maintained at 0.7 MPa, such that an aqueous solution of caprolactam crystal was contacted with hydrogen gas to perform reaction for 1 hour. The evaporation and dehydration process was then performed on a rotary evaporator (−0.09 MPa, 80° C.), the vacuum distillation was then performed at about 1 mmHg to obtain 130 g of caprolactam product, the distillation process was stopped. The quality of obtained caprolactam product was analyzed, wherein the caprolactam purity was 99.9945%, the PM value was 39600 s, the VB was 0.050 mmol/kg, the E value was 0.034, the chroma value was 0, and the alkalinity was 0.03 mmol/kg.

EXAMPLE 2

The preparation process of crude caprolactam in the example 2 was performed according to the same process as in the preparation example 1, except that the treatment methods of dehydration and removing light impurities adopted in example 2 were different from those of the preparation example 1, and the other treatment methods were the same as those of the preparation example 1, the example 2 specifically used the following treatment methods of dehydration and removing light impurities: the crude caprolactam product of the preparation example 1 was subjected to the vacuum distillation (16 tower trays and inverted triangular metal packing) at a pressure (absolute pressure) of 1.3 kPa and heated from room temperature (20° C.) to 90° C. at a temperature rise rate of 3° C./min and the temperature 90° C. was kept for 40 min, there was not reflux on the tower top, the temperature was further increased to 160° C. at a temperature rise rate of 3° C./min, and the pressure was decreased directly to 0.35 kPa, the tower top reflux ratio was 1:40 until there was no light components were distilled to produce 264.6 g of product obtained after removing light component (kettle bottom material, i.e., crude caprolactam). The crude caprolactam was subjected to the chromatographic analysis, the analysis result indicated that the crude caprolactam was consisting of the main components as follows: 98.9 wt % of caprolactam, 190 µg/g of 5-cyano-1-pentene, 200 µg/g of cyclohexanone oxime, 1,000 µg/g of cyclohexenone, 460 µg/g of 1,2,3,4,5,6,7,8-octahydrophenazine, 520 µg/g of 1,3,4,5-tetrahydro-2H-azepin-2-one and isomers thereof, and 1,180 µg/g of decahydrophenazine.

The crude caprolactam obtained in the example was subjected to the refining process as follows:

(1) First evaporative crystallization: the crude caprolactam (300 parts by weight) prepared and obtained from the example and a mixed solvent (900 parts by weight) consisting of 18 parts by weight of ethanol and 882 parts by weight of n-heptane were sufficiently blended in an adiabatic glass crystallization kettle (i.e., a first evaporative crystallizer), the crude caprolactam was thoroughly dissolved in the mixed solvent with a temperature of 65° C., when the temperature inside the crystallization kettle was slowly decreased to 61° C., 2 wt % of pure caprolactam at 20-30 meshes was added into the solution as the seed crystal, the vacuumization process was started in the crystallization kettle, an evaporative crystallization was performed, the operating pressure was 50 kPa, the amount of evaporation was controlled, the solvent was uniformly evaporated; while the solvent was continuously volatilized, the temperature of the liquid phase in the crystallization kettle was decreased accordingly; when the temperature of the crystallization kettle was decreased to 58° C., the caprolactam started to precipitate, the solvent was continuously extracted, the operating pressure was continuously adjusted; when the temperature of the solution in the crystallization kettle was decreased to 45° C., the operating pressure was controlled to be 20 kPa (i.e., the final vacuum degree or final pressure), the solvent was further extracted; when the temperature of the solution inside the crystallization kettle was lowered to 40° C. (i.e., the final temperature), the vacuumization was stopped, the temperature was maintained at 40° C. for 60 min, and the experiment was terminated.

(2) First solid-liquid separation, first washing: the caprolactam slurry obtained in step (1) (i.e., a first slurry, 1,200 parts by weight) was pumped from the crystallizer to a centrifuge (i.e., a first solid-liquid separation device and a first washing device) to perform a first solid-liquid separation, in order to obtain a first caprolactam crystal and a first crystallization mother liquor. The solid phase obtained in step (1) (i.e., a first caprolactam crystal) was washed with the mixed solvent (250 parts by weight; with the same temperature as the final temperature of first evaporative crystallization) consisting of the same components in the same proportions as defined above, the solid-liquid separation was then continued to obtain a caprolactam crystal (i.e., a second caprolactam crystal, 247 parts by weight) and a liquid phase (i.e., a first washing liquid, 1,200 parts by weight).

(3) Second evaporative crystallization and second solid-liquid separation, second washing and thermostatic crystallization: the first crystallization mother liquor was subjected to the second evaporative crystallization and the second solid-liquid separation, the second washing, and the thermostatic crystallization in sequence according to the process of steps (3)-(5) of example 1. The overall yield of caprolactam was 99.2%.

(4) Hydrogenation reaction: 150 g of the caprolactam crystal (i.e., the second caprolactam crystal with a purity of 99.9916 wt %) was added to a 500 mL reaction kettle (i.e., a hydrogenation reactor) and 37.5 g of water was added, 1.5 g of an amorphous nickel hydrogenation catalyst (manufactured by the Sinopec Catalyst Changling Branch with the industrial trade name SRNA-4) was further added, the mixture was heated to about 75° C., hydrogen gas was then introduced, the hydrogen gas flow rate was controlled at 100 mL/min, the reaction pressure was maintained at 0.7 MPa, such that an aqueous solution of caprolactam crystal was contacted with hydrogen gas to perform reaction for 1 hour. The evaporation and dehydration process was then performed on a rotary evaporator (−0.09 MPa, 100° C.), the vacuum distillation was then performed at about 1mmHg to obtain 130 g of caprolactam product, the distillation process was stopped. The quality of obtained caprolactam product was analyzed, wherein the caprolactam purity was 99.9923%, the PM value was 36000 s, the VB was 0.065 mmol/kg, the E value was 0.036, the chroma value was 1, and the alkalinity was 0.046 mmol/kg.

EXAMPLE 3

The preparation process of the crude caprolactam used in the examples was identical with that in the example 2.

(1) First evaporative crystallization: the crude caprolactam (300 parts by weight) and a mixed solvent (in a total of 900 parts by weight, wherein the ratio of cyclohexane to n-heptane was 1:3) consisting of 9 parts by weight of ethanol, 223 parts by weight of cyclohexane and 668 parts by weight of n-heptane were sufficiently blended in an adiabatic glass crystallization kettle (i.e., a first evaporative crystallizer), the crude caprolactam was thoroughly dissolved in the mixed solvent with a temperature of 65° C., when the temperature inside the crystallization kettle was slowly decreased to 61° C., 2 wt % of pure caprolactam at 20-30 meshes was added into the solution as the seed crystal, the vacuumization process was started in the crystallization kettle, an evaporative crystallization was performed, the operating pressure was 50 kPa, the amount of evaporation was controlled, the solvent was uniformly evaporated; while the solvent was continuously volatilized, the temperature of the liquid phase in the crystallization kettle was decreased accordingly; when the temperature of the crystallization kettle was decreased to 58° C., the caprolactam started to precipitate, the solvent was continuously extracted, the operating pressure was continuously adjusted; when the temperature of the solution in the crystallization kettle was decreased to 45° C., the operating pressure was controlled to be 20 kPa (i.e., the final vacuum degree or final pressure), the solvent was further extracted; when the temperature of the solution inside the crystallization kettle was lowered to 40° C. (i.e., the final temperature), the vacuumization was stopped, the temperature was maintained at 40° C. for 60 min, and the experiment was terminated.

(2) The first solid-liquid separation, the first washing: the caprolactam slurry obtained in step (1) (i.e., a first slurry, 1,200 parts by weight) was pumped from the crystallizer to a centrifuge (i.e., a first solid-liquid separation device and a first washing device) to perform a first solid-liquid separation, in order to obtain a first caprolactam crystal and a first crystallization mother liquor. The solid phase obtained in step (1) (i.e., a first caprolactam crystal) was washed with the mixed solvent (240 parts by weight; with the same temperature as the final temperature of first evaporative crystallization) consisting of the same components in the same proportions as defined above, the solid-liquid separation was then continued to obtain a caprolactam crystal (i.e., a second caprolactam crystal, 245 parts by weight) and a liquid phase (i.e., a first washing liquid, 1,200 parts by weight).

(3) The second evaporative crystallization and the second solid-liquid separation, the second washing and the thermostatic crystallization: the first crystallization mother liquor was subjected to the second evaporative crystallization and the second solid-liquid separation, the second washing, and the thermostatic crystallization in sequence according to the process of steps (3)-(5) of example 1. The overall yield of caprolactam was 99.4%.

(4) Hydrogenation reaction: 150 g of the caprolactam crystal (i.e., the second caprolactam crystal with a purity of 99.9920 wt %) was added to a 500 mL reaction kettle (i.e., a hydrogenation reactor) and 150 g of water was added, 1.5 g of an amorphous nickel hydrogenation catalyst (manufactured by the Sinopec Catalyst Changling Branch with the industrial trade name SRNA-4) was further added, the mixture was heated to about 75° C., hydrogen gas was then introduced, the hydrogen gas flow rate was controlled at 100 mL/min, the reaction pressure was maintained at 0.7 MPa, such that an aqueous solution of caprolactam crystal was contacted with hydrogen gas to perform reaction for 1 hour. The evaporation and dehydration process was then performed on a rotary evaporator (−0.09 MPa, 80° C.), the vacuum distillation was then performed at about 1 mmHg to obtain 130 g of caprolactam product, the distillation process was stopped. The quality of obtained caprolactam product was analyzed, wherein the caprolactam purity was 99.9931%, the PM value was 36000 s, the VB was 0.058 mmol/kg, the E value was 0.030, the chroma value was 0, and the alkalinity was 0.035 mmol/kg.

EXAMPLE 4

The preparation process of the crude caprolactam used in the examples was identical with that in the example 2.

(1) First evaporative crystallization: the crude caprolactam (300 parts by weight) and a mixed solvent (900 parts by weight) consisting of 14 parts by weight of ethanol, 886 parts by weight of 2-chloro-butane were sufficiently blended in an adiabatic glass crystallization kettle (i.e., a first evaporative crystallizer), the crude caprolactam was thoroughly dissolved in the mixed solvent with a temperature of 60° C., when the temperature inside the crystallization kettle was slowly decreased to 60° C., the vacuumization process was started in the crystallization kettle, an evaporative crystallization was performed, the operating pressure was 50 kPa, the amount of evaporation was controlled, the solvent was uniformly evaporated; while the solvent was continuously volatilized, the temperature of the liquid phase in the crystallization kettle was decreased accordingly; when the temperature of the crystallization kettle was decreased to 45° C., the operating pressure was controlled to be 40 kPa; when the temperature of the crystallization kettle was decreased to 42° C., 2 wt % of pure caprolactam at 20-30 meshes was added into the solution as the seed crystal, the caprolactam started to precipitate at a temperature of 41° C., the solvent was continuously extracted, the operating pressure was continuously adjusted according to the actual condition; when the temperature of the solution in the crystallization kettle was decreased to 35° C., the operating pressure was controlled to be 22 kPa (i.e., the final vacuum degree or final pressure), the solvent was further extracted; when the temperature of the solution inside the crystallization kettle was lowered to 30° C. (i.e., the final temperature), the vacuumization was stopped, the temperature was maintained at 30° C. for 45 min, and the experiment was terminated.

(2) First solid-liquid separation, first washing: the caprolactam slurry obtained in step (1) (i.e., a first slurry, 1,200 parts by weight) was pumped from the crystallizer to a centrifuge (i.e., a first solid-liquid separation device and a first washing device) to perform a first solid-liquid separation, in order to obtain a first caprolactam crystal and a first crystallization mother liquor. The solid phase obtained in step (1) (i.e., first caprolactam crystal) was washed with the mixed solvent (220 parts by weight; with the same temperature as the final temperature of first evaporative crystallization) consisting of the same components in the same proportions as defined above, the solid-liquid separation was then continued to obtain a caprolactam crystal (i.e., a second caprolactam crystal, 223 parts by weight) and a liquid phase (i.e., a first washing liquid, 1,200 parts by weight).

(3) The second evaporative crystallization and the second solid-liquid separation, the second washing and the thermostatic crystallization: the first crystallization mother liquor was subjected to the second evaporative crystallization and the second solid-liquid separation, the second washing, and the thermostatic crystallization in sequence according to the process of steps (3)-(5) of example 1. The overall yield of caprolactam was 99.1%.

(4) Hydrogenation reaction: 150 g of the caprolactam crystal (i.e., the second caprolactam crystal) was added to perform the hydrogenation reaction according the same process as that in the Example 3.140 g of caprolactam product was obtained, the distillation process was then stopped. The quality of obtained caprolactam product was analyzed, wherein the caprolactam purity was 99.9936%, the PM value was 36000 s, the VB was 0.055 mmol/kg, the E value was 0.032, the chroma value was 0, and the alkalinity was 0.033 mmol/kg.

EXAMPLE 5

The preparation process of the crude caprolactam used in the examples was identical with that in the example 1, except that during the first evaporative crystallization process in step (1), the same amount of the crude caprolactam produced in the preparation example 2 was used for replacing the crude caprolactam produced in the preparation example 1, the other components and steps were identical with those of the example 1.

The yield of the caprolactam product was 98.7%. The quality of obtained caprolactam product was analyzed, wherein the caprolactam purity was 99.9944%, the PM value was 39600 s, the VB was 0.050 mmol/kg, the E value was 0.034, the chroma value was 0, and the alkalinity was 0.03 mmol/kg.

EXAMPLE 6

The preparation process of the crude caprolactam used in the examples was identical with that in the example 1, except that in step (1), the ethanol was not added, but 900 parts by weight of isopropyl ether was used; and in step (3), the first crystallization mother liquor was concentrated, ethanol was then added such that the caprolactam concentration was 10.5 wt %, the ethanol content in the second evaporative crystallization solvent was 1 wt %, the second evaporative crystallization was subsequently carried out, the other components and steps were identical with those of the example 1.

The yield of the caprolactam product was 99.3%. The quality of obtained caprolactam product was analyzed, wherein the caprolactam purity was 99.9944%, the PM value was 39600 s, the VB was 0.050 mmol/kg, the E value was 0.034, the chroma value was 2, and the alkalinity was 0.03 mmol/kg.

By using the process provided by the present disclosure, caprolactam is prepared with a relatively high yield while ensuring high purity of the caprolactam. In addition, a use of the preferred embodiment of the present disclosure allows that the superior crystallization is obtained by adopting a particular ethanol-containing mixed solvent system for performing crystallization of crude caprolactam product obtained from gas phase Beckmann rearrangement of cyclohexanone oxime under the condition of using ethanol as the solvent.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A process for refining caprolactam comprising the following steps:
   (1) subjecting a crude caprolactam having a caprolactam content not less than 98 wt % to a first evaporative crystallization in the presence of a first crystallization solvent, so as to obtain a first slurry;
   (2) subjecting the first slurry to a first solid-liquid separation to obtain a first caprolactam crystal and a first crystallization mother liquor;
   (3) subjecting the first caprolactam crystal to a first washing to obtain a second caprolactam crystal and a first washing liquid;
   (4) optionally concentrating the first crystallization mother liquor and then subjecting the concentrated first crystallization mother liquor to a second evaporative crystallization to obtain a second slurry;
   (5) subjecting the second slurry to a second solid-liquid separation to obtain a third caprolactam crystal and a second crystallization mother liquor;
   (6) subjecting the third caprolactam crystal to a second washing to obtain a fourth caprolactam and a second washing liquid;

(7) optionally concentrating the second crystallization mother liquor, then subjecting the concentrated second crystallization mother liquor to a thermostatic crystallization to obtain a third slurry, which is subjected to a third solid-liquid separation to obtain a fifth caprolactam crystal and a third crystallization mother liquor;

(8) subjecting the fifth caprolactam crystal to a third washing to obtain a sixth caprolactam crystal and a third washing liquid; and (9) subjecting the second caprolactam crystal obtained in step (3) to a hydrogenation reaction;

wherein the thermostatic crystallization is carried out in the presence of a thermostatic crystallization solvent comprising solvent A and ethanol, the solubility of caprolactam in solvent A at a temperature of 20° C. is less than 5 wt %, and ethanol is less than 2 wt % of the total amount of thermostatic crystallization solvent.

2. The process of claim 1, wherein the second evaporative crystallization has a final temperature that is 5-20° C. lower than the final temperature of the first evaporative crystallization; and/or the second evaporative crystallization has a vacuum degree that is 5-20 kPa lower than the vacuum degree of the first evaporative crystallization.

3. The process of claim 1, wherein the conditions for the first evaporative crystallization comprise a final temperature within a range of 10-65° C. and a vacuum degree of 5-80 kPa; and/or the conditions of the second evaporative crystallization comprise a final temperature within a range of 5-60° C. and a vacuum degree of 0-70 kPa.

4. The process of claim 1, wherein the first crystallization solvent in step (1) is used in an amount such that the solid content of caprolactam in a mixture of the crude caprolactam and the first crystallization solvent is 35 wt % or less; and/or the first crystallization mother liquor in step (4) is subjected to concentrating, which causes that the obtained product has a solid content of caprolactam being 15 wt % or more.

5. The process of claim 1, wherein ethanol is 0.5-2 wt % of the total amount of the thermostatic crystallization solvent; and/or the first crystallization solvent comprises a solvent A, which is at least one selected from the group consisting of halogenated hydrocarbons, ethers, and alkanes having 6-12 carbon atoms; and/or the first crystallization solvent further comprises ethanol, which is 2 wt % or less of the total amount of the first crystallization solvent.

6. The process of claim 1, wherein the solvent A is at least one selected from the group consisting of isopropyl ether, n-heptane, isooctane, sec-butylchloride and cyclohexane.

7. The process of claim 1, wherein the temperature of the first washing in step (3) is not lower than the final temperature of the first evaporative crystallization; and/or the weight ratio of the used amount of washing solvent in the first washing relative to the first caprolactam crystal is 0.5-1.5:1; and/or the washing solvent used in the first washing is identical with the first crystallization solvent.

8. The process of claim 1, wherein the temperature of the second washing in step (6) is not lower than the final temperature of the second evaporative crystallization; and/or the weight ratio of the used amount of washing solvent in the second washing relative to the third caprolactam crystal is 0.5-1.5:1.

9. The process of claim 1, wherein the temperature of third washing in step (8) is not lower than the thermostatic crystallization; and/or the weight ratio of the used amount of washing solvent in the third washing relative to the fifth caprolactam crystal is 0.5-1.5:1.

10. The process of claim 1, wherein the washing solvents used in the second washing and the third washing are respectively and independently identical with the first crystallization solvent and/or the thermostatic crystallization solvent.

11. The process of claim 1, wherein the process further comprises: recycling the first washing liquid to provide at least one of the following components: at least a portion of the first crystalline solvent, the washing solvent used in the second washing, and the washing solvent used in the third washing; and/or the process further comprises: recycling the second washing liquid to provide at least a portion of the washing solvent used in the third washing; and/or the process further includes: mixing the third washing liquid with the second crystallization mother liquor to jointly carry out the thermostatic crystallization.

12. The process of claim 1, wherein the temperature of said thermostatic crystallizationin in step (7) is lower than the final temperature of said second evaporative crystallization.

13. The process of claim 1, wherein the conditions of thermostatic crystallization comprise a temperature within a range of 5-50° C.; and/or the second crystallization mother liquor in step (7) is subjected to concentrating, which causes that the obtained product has a solid content of caprolactam within a range of 15-30 wt %.

14. The process of claim 1, wherein the hydrogenation reaction in step (9) is performed in the presence of water and a hydrogenation catalyst.

15. The process of claim 14, wherein the used amount of water is 10-200 parts by weight relative to 100 parts by weight of the second caprolactam crystal; and/or the hydrogenation catalyst is at least one selected from the group consisting of a nickel based catalyst, a palladium based catalyst, and a platinum based catalyst; and/or the conditions of hydrogenation reaction comprises a temperature of 50-150° C., a pressure of 0.2-2 MPa, and the hydrogen is used in an amount of 0.01-0.25 mole relative to 1 mole of the second caprolactam crystal.

16. The process of claim 1, wherein the process further comprises recycling the fourth caprolactam and the sixth caprolactam crystal to step (1) in admixture with the crude caprolactam to perform the first evaporative crystallization; and/or the process further comprises: recovering solvent from the third crystallization mother liquor.

17. The process of claim 1, wherein the crude caprolactam is obtained from the gas phase Beckmann rearrangement reaction product of cyclohexanone oxime through the steps of solvent recovery, dehydration and removing the light component; and/or the solvent for the gas phase Beckmann rearrangement reaction of cyclohexanone oxime is ethanol.

18. The process of claim 1, wherein the crude caprolactam of step (1) further comprises at least one selected from the group consisting of cyclohexene, cyclohexadiene, acetonitrile, ethyl-acrylonitrile, propionitrile, ethoxy-cyclohexene, butyronitrile, ethyl-valeronitrile, cyclopentanone, ethyl cyclopentanone, valeronitrile, ethyl pyridine, ethyl hexenoate, ethoxy-1,3-cyclohexadiene, ethoxy-1,4-cyclohexadiene, cyclohexanone, hexanenitrile, cyanocyclopentane, ethyl-ε-hexylimide, ethyl-cyclohexanone, 5-cyano-1-pentene, ethoxy-cyclohexanone, cyclohexenone, cyclohexanol, phenol, bicyclo[3.1.0]-pentanone-2, N,N-diethyl-aniline, N-ethyl-aniline, phenylamine, ethyl-aniline, N-hexanamide, N-valeramide, valerolactam, N-ethyl-caprolactam, 1,2,3,4,5,6,7,8-octahydroacridine, 1,2,3,4,5,6,7,8-octahydrophenazine, decahydrophenazine, 1,3,4,5-tetrahydro-2H-azepin-2-one and isomers thereof, 5,6,7,8-tetrahydro-2-naphthylamine and 1,2,3,4-tetrahydrocarbazole; and/or wherein the content of caprolactam is 98-99 wt %, the content of 1,2,3,4,5,6,7,8-octahydrophenazine is 0.01-0.3 wt %, the content of decahydrophenazine is 0.1-0.3 wt %, the content of 1,3,4,5-tetrahydro-2H-azepin-2-one and isomers thereof is 0.01-0.1 wt %, based on the total amount of the crude caprolactam.

19. A refining system of caprolactam comprising a first evaporative crystallizer, a first solid-liquid separation device and a first washing device connected in series, wherein an outlet of the first evaporative crystallizer is in communication with an inlet of the first solid-liquid separation device, and the solid phase outlet of the first solid-liquid separation device is in communication with an inlet of the first washing device;

the system further comprises a second evaporative crystallizer, a second solid-liquid separation device and a second washing device successively connected in series, wherein an inlet of the second evaporative crystallizer is in communication with the liquid phase outlet of the first solid-liquid separation device, an outlet of the second evaporative crystallizer is in communication with an inlet of the second solid-liquid separation device, and a solid phase outlet of the second solid-liquid separation device is in communication with an inlet of the second washing device; optionally a first solvent recovery column is disposed at the communication pipeline between an inlet of the second evaporative crystallizer and the liquid phase outlet of the first solid-liquid separation device;

the system further comprise a thermostatic crystallizer, a third solid-liquid separation device and a third washing device connected in series, wherein an inlet of the thermostatic crystallizer is in communication with the liquid phase outlet of the second solid-liquid separation device, an outlet of the thermostatic crystallizer is in communication with an inlet of the third solid-liquid separation device, the solid phase outlet of the third solid-liquid separation device is in communication with an inlet of the third washing device; optionally a second solvent recovery column is arranged at the communication pipeline between an inlet of the thermostatic crystallizer and the liquid phase outlet of the second solid-liquid separation device;

the system further comprise a hydrogenation reactor, an inlet of the hydrogenation reactor is in communication with the solid phase outlet of the first washing device.

20. The refining system of claim 19, wherein the liquid phase outlet of the first washing device is in communication with an inlet of the first evaporative crystallizer and/or the second washing device; and/or the liquid phase outlet of the second washing device is in communication with an inlet of the third washing device; and/or the liquid phase outlet of said third washing device is in communication with the thermostatic crystallizer; and/or the solid phase outlet of the second washing device and the solid phase outlet of the third washing devices are respectively in communication with an inlet of the first evaporative crystallizer.

* * * * *